US008318419B2

(12) United States Patent
Summers et al.

(10) Patent No.: US 8,318,419 B2
(45) Date of Patent: Nov. 27, 2012

(54) ANTIVIRAL SCREENING METHOD TO IDENTIFY INHIBITORS OF PHOSPHATIDYLINOSITOL 4,5-BISPHOSPHATE [PI(4,5)P$_2$] BINDING TO THE HIV GAG MATRIX (MA) PROTEIN

(75) Inventors: Michael F. Summers, Ellicott City, MD (US); Jamil S. Saad, Hoover, AL (US)

(73) Assignee: University of Maryland, Baltimore County, Baltimore, MD (US)

( * ) Notice: Subject to any disclaimer, the term of this patent is extended or adjusted under 35 U.S.C. 154(b) by 246 days.

(21) Appl. No.: 12/175,809

(22) Filed: Jul. 18, 2008

(65) Prior Publication Data
US 2009/0023161 A1 Jan. 22, 2009

Related U.S. Application Data

(60) Provisional application No. 60/961,328, filed on Jul. 20, 2007.

(51) Int. Cl.
*C12Q 1/70* (2006.01)
*A61K 39/21* (2006.01)
*C07K 1/00* (2006.01)

(52) U.S. Cl. .......................... 435/5; 424/208.1; 530/350

(58) Field of Classification Search .................. None
See application file for complete search history.

(56) References Cited

U.S. PATENT DOCUMENTS

| | | | |
|---|---|---|---|
| 7,183,300 | B2 | 2/2007 | Summers et al. |
| 7,361,459 | B2 | 4/2008 | Summers et al. |
| 2004/0265320 | A1 | 12/2004 | Salzwedel et al. |
| 2005/0015039 | A1 | 1/2005 | Salzwedel et al. |
| 2008/0200550 | A1 | 8/2008 | Salzwedel et al. |
| 2008/0233559 | A1 | 9/2008 | Salzwedel et al. |

OTHER PUBLICATIONS

Shkriabai, N., et al., 2006, Interactions of HIV-1 Gag with assembly cofactors, Biochem. 45:4077-4083 (available Mar. 14, 2006).*
Saad, J. S., et al., 2006, Structural basis for targeting HIV-1 Gag proteins to the plasma membrane for virus assembly, Proc. Natl. Acad. Sci. USA 103(30):11364-11369 (available Jul. 13, 2006).*
Ono, A., Phosphatidylinositol (4,5) bisphosphate regulates HIV-1 Gag targeting to the plasma membrane, Proc. Natl. Acad. Sci. USA 101(41):14889-14894.*
Xu, Y., et al., 2006, Evaluation of "credit card" libraries for inhibition of HIV-1 gp41 fusogenic core formation, J. Comb. Chem. 8:531-539 (available Apr. 22, 2006).*
McMahon, J. B., et al., 2000, Development of a cyanovirin-N-HIV-1 gp120 binding assay for high throughput screening of natural product extracts by time-resolved fluorescence, J. Biomol. Screen. 5(3):169-176.*
Saad, J. S., et al., Jul. 25 2006, Structural basis for targeting HIV-1 Gag proteins to the plasma membrane for virus assembly, Proc. Natl. Acad. Sci. 103(30):11364-11369.*
Chan, J., et al., Oct. 2011, Rous sarcoma virus Gag has not specific requirement for phosphatidylinositol-(4,5)-bisphosphate for plasma membrane association in vivo or for liposome interaction in vitro, J. Virol. 85(20):10851-10860.*
Saad, J. S., et al., 2007, Point mutations in the HIV-1 matrix protein turn off the myristyl switch, J. Mol. Biol. 366:574-585.*
Lee, Y.-M., et al., Feb. 1997, Mutations in the matrix protein of human immunodeficiency virus type 1 inhibit surface expression and virion incorporation of viral envelope glycoproteins in CD4+ T lymphocytes, J. Virol. 71(2):1443-1452.*
McMahon, J. B., et al., 2000, Development of a cyanovirin-N-HIV-1 gp120 binding assay for high throughput screening of natural product extracts by time-resolved fluorescence, J. Biomolec. Screening 5(3):169-176.*
Gheysen D., Jacobs E., de Foresta F., Thiriart C., Francotte M., Thines D., De Wilde M. Assembly and Release of HIV-1 Precursor PRSS Virus-like Particles from Recombinant Baculovirus-Infected Insect Cells. *Cell.* 1989;59:103-112.
Wills J., Craven R. Form, function and use of retroviral Eng proteins. *Aids.* 1991;5:639-654.
Freed E. O. HIV-1 Gag Proteins: Diverse Functions in the Virus Life Cycle. *Virology.* 1998;251:1-15.
Briggs J. A. G., Simon M. N., Gross I., Krausslich H.-G., Fuller S. D., Vogt V. M., Johnson M. C. The stoichiometry of Gag protein in HIV-1. *Nat. Struct. Mol. Biol.* 2004;11:672-675.
Vogt V. M., Simon M. N. Mass Determination of Rovs Sarcoma Virus Virions by Scanning Transmission Electron Microscopy. *J. Virol.* 1999;73:7050-7055.
Bryant M., Ratner L. Myristoylation-dependant replication and assembly of human immunodeficiency virus 1. *Proc. Natl. Acad. Sci. USA.* 1990;87:523-527.
Copeland N. G., Jenkins N. A., Nexo B., Schultz A. M., Rein A., Mikkelsen T., Jorgensen P. Poorly Expressed Endogenous Ecotropic Provirus of DBA/2 Mice Encodes a Mutant Pr65 Protein that is not Myristylated. *J. Virol.* 1988;62:479-487.
Göttlinger H. G., Sodroski J. G., Haseltine W. A. Role of capsid precursor processing and myristoylation in morphogensis and infectivity of human immunodeficiency virus type 1. *Proc. Natl. Acad. Sci. USA.* 1989;86:5781-5785.
Spearman P., Horton R., Ratner L., Kuli-Zade I. Membrane binding of human immunodeficiency virus type 1 matrix protein in vivo supports a conformational myristyl switch mechanism. *J. Virol.* 1997;71:6582-6592.

(Continued)

*Primary Examiner* — Jeffrey S. Parkin
(74) *Attorney, Agent, or Firm* — Marianne Fuierer; Moore & Van Allen, PLLC

(57) ABSTRACT

The present invention provides for testing methods to determine an effective testing agent that affects the activity of the HIV Gag protein at the plasma membrane of a cell, and specifically, effecting changes in the structural conformation of at least one fatty acid of PI(4,5)P$_2$, a member of a family of differentially phosphorylated phosphatidylinositides, wherein inhibition of the extension of such fatty acid into the MA domain of the Gag protein reduces binding of Gag to the plasma membrane, thereby inhibiting virus particle assembly and subsequent replication of the HIV virus.

10 Claims, 14 Drawing Sheets

OTHER PUBLICATIONS

Spearman P., Wang J.-J., Vander Heyden N., Ratner L. Identification of Human Immunodeficiency virus type 1 Gag Protein Domains Essential to Membrane Binding and Particle Assembly. *J. Virol.* 1994;68:3232-3242.

Yuan X., Yu X., Lee T.-H., Essex M. Mutations in the N-Terminal Region of Human Immunodeficiency Virus Type 1 Matrix Protein Block Intracellular Transport of Gag Precursor. *J. Virol.* 1993;67:6387-6394.

Freed E. O., Orenstein J. M., Buckler-White A. J., Martin M. A. Single Amino Acid Changes in the Human Immunodeficiency Virus Type 1 Matrix Protein Block Virus Particle Production. *J. Virol.* 1994;68:5311-5320.

Ono A., Orenstein J. M., Freed E. O. Role of the Gag Matrix Domain in Targeting Human Immunodeficiency Virus Type 1 Assembly. *J. Virol.* 2000;74:2855-2866.

Hermida-Matsumoto L., Resh M. D. Localization of Human Immunodeficiency Virus Type 1 Ggg and Env at the Plasma Membrane by Confocal Imaging. *J. Virol.* 2000;74:8670-8679.

Zhou W., Resh M. D. Differential Membrane Binding of the Human Immunodeficiency Virus Type 1 Matrix Protein. *J. Virol.* 1996;70:8540-8548.

Paillart J.-C., Gottlinger H. G. Opposing Effects of Human Immunodeficiency Virus Type 1 Matric Mutations Support a Myristyl Switch Model of Gag Membrane Targeting. *J. Virol.* 1999;73:2604-2612.

Hermida-Matsumoto L., Resh M. D. Human Immunodeficiency Virus Type 1 Protease Triggers a Myristoyal Switch that Modulates Membrane Binding of Pr55 and p17MA. *J. Virol.* 1999;73:1902-1908.

Bouamr F., Scarlata S., Carter C. A. Role of Myristylation in HIV-1 Gag Assembly. *Biochemistry.* 2003;42:6408-6417.

Tang C., Loeliger E., Luncsford P., Kinde I., Beckett D., Summers M. F. Entropic Switch Regulates Myristate Exposure in HIV-1 Matrix Protein. *Proc. Natl. Acad. Sci. USA.* 2004;101:517-522.

Cannon P. M., Matthews S., Clark N., Byles E. D., Iourin O., Hockley D. J., Kingsman S., Kingsman A. Structure-Function Studies of the Human Immunodeficiency Virus Type 1 Matrix Protein, p17. *J. Virol.* 1997;71:3474-3483.

Ono A., Ablan S. D., Lockett S. J., Nagashima K., Freed E. O. Phosphatidylinositol (4,5) biphospate regulates HIV-1 Gag Targeting to the Plasma Membrane. *Proc. Natl. Acad. Sci. USA.* 2004;101:14889-14894.

Dong X., Li H., Derdowski A., Ding L., Burnett A., Chen X., Peters T. R., Dermody T. S., Woodruff E., Wang J.-J., Spearman P. AP-3 Directs the Intracellular Traficking of HIV-1 Gag and Plays a Key Role in Particle Assembly. *Cell.* 2005;120:663-674.

Nguyen D. G., Booth A., Gould S. J., Hildreth J. E. J. Evidence that HIV Budding in Primary Macrophages Occurs through the Exosome Release Pathway. *Biol. Chem.* 2003;278:52347-52354.

* cited by examiner

ANTIVIRAL SCREENING METHOD TO IDENTIFY INHIBITORS OF PHOSPHATIDYLINOSITOL 4,5-BISPHOSPHATE [PI(4,5)P$_2$] BINDING TO THE HIV GAG MATRIX (MA) PROTEIN

CROSS-REFERENCE TO RELATED APPLICATIONS

This application claims priority to U.S. Provisional Application No. 60/961,328 filed in the United States Patent and Trademark Office on Jul. 20, 2007, the contents of which are hereby incorporated by reference herein for all purposes.

GOVERNMENT RIGHTS IN INVENTION

Work related to the invention was conducted in the performance of a grant from National Institute of Health with a grant number AI30917 and as a result, the U.S. Government has certain rights in the invention described herein.

BACKGROUND OF THE INVENTION

1. Field of the Invention

The present invention generally relates to methods of drug screening and treating HIV, and more particularly, to inhibiting the binding of the HIV gag protein with the plasma membrane of an infected cell thereby reducing replication of the HIV virus.

2. Related Art

Human immunodeficiency virus (HIV) infection causes the acquired immunodeficiency syndrome (commonly known as AIDS). HIV is a retrovirus that primarily infects T cells expressing the CD4 glycoprotein, i.e., CD4$^+$ T-cells, which are also known as helper T-cells. HIV virus multiplies in helper T-cells and quickly destroys the host helper T-cells, resulting in cellular immunity depression and leaving the infected patient susceptible to opportunistic infections, malignancies and various other pathological conditions. Ultimately, HIV infection can cause depletion of helper T-cells and collapse of a patient's immune defenses. Not surprisingly, HIV-infected individuals and AIDS patients typically develop AIDS-related conditions such as AIDS-related complex (ARC), progressive generalized lymphadenopathy (PGL), dementia, tropical paraparesis, Kaposi's sarcoma, thrombocytopenia purpurea, herpes infection, cytomegalovirus infection, Epstein-Barr virus related lymphomas among others.

HIV is a nontransforming human retrovirus belonging to the lentivirus family. Two genetically different but related forms of HIV, called HIV-1 and HIV-2, have been isolated from patients with AIDS. HIV-1 is the most common type associated with AIDS in the United States, Europe, and Central Africa, whereas HIV-2 causes similar disease principally in West Africa.

Retroviral genomes encode a polyprotein called Gag that contains all of the viral elements required for virus assembly (1). Subsequent to ribosomal synthesis, the Gag proteins are directed to punctuate sites on plasma and/or endosomal membranes, where they assemble and bud to form immature virions (2-4). Approximately 1,500-5,000 copies of Gag contribute to each virus particle (4, 5). During or shortly after budding, the Gag proteins are cleaved by the viral protease into the matrix (MA), capsid (CA), and nucleocapsid proteins, which rearrange to form mature and infectious virions.

Membrane binding is mediated by Gag's N-terminal MA domain and, for most retroviruses, depends on posttranscriptional N-terminal acylation. The MA domain of HIV [types HIV-1 and 2] requires an N-terminal myristyl group that functions in concert with a group of conserved basic residues to promote membrane selection and binding. Mutations that either block myristoylation (6-10) or disrupt the basic patch (11-14) inhibit membrane binding in vitro and can lead to aberrant targeting of Gag to the cytoplasm and/or intracellular membranes in vivo. Intact Gag binds more tightly to membranes than the isolated MA protein, which led to the suggestion that binding may be mediated by a myristyl switch mechanism (9, 15-18). Consistent with this hypothesis, NMR-based structural studies confirmed that the myristyl group of MA can adopt myristate sequestered [myr(s)] and exposed [myr(e)] conformations, and that protein self association promotes myristate exposure (19).

The ability of HIV-1 Gag to colocalize at specific subcellular membranes is essential for viral replication and pathogenesis and may be important for establishing intracellular viral reservoirs that are protected from the immune system (13, 14, 20-25). In most hematopoietic cells, Gag molecules assemble and bud from the plasma membrane (PM), possibly by indirect routing by endosome/multivesicular body (MVB) compartments (14, 22). Gag may also be transiently routed through the nucleus before assembly (26-28). In primary macrophages, budding occurs mainly in MVBs (22-25). Recent studies indicate that the ultimate localization of Gag at virus assembly sites depends on phosphatidylinositol (PI)4, 5-bisphosphate [PI(4,5)P$_2$ (21), a member of a family of differentially phosphorylated phosphatidylinositides that serve as membrane markers for specific cellular proteins (29-31). PI(4,5)P$_2$ is normally associated with the inner leaflet of the PM (30). Depletion of PI(4,5)P$_2$ inhibits virus assembly and leads to accumulation of Gag at the membranes of late endosomes and MVBs. Induction of PI(4,5)P$_2$-enriched endosomes also retargets Gag to endosome/MVBs and induces intravesicle budding. In both cases, virus production is severely attenuated (21). Substitution of MA by the membrane-binding N terminus of Fyn kinase reduces the sensitivity of virus assembly to PI(4,5)P$_2$ manipulation, suggesting that PI(4,5)P$_2$-dependent membrane selection is mediated by the MA domain of Gag (21). Consistent with this hypothesis it has been recently shown that phosphoinositides are capable of binding to the MA domain of unmyristoylated Gag fragments and promoting their assembly in vitro into virus-like particles (32, 33).

There has been a great deal of effort in developing methods and pharmaceutical compounds for treating HIV infection and AIDS. The therapeutic approaches have been mostly focused on a limited number of drug targets, namely HIV reverse transcriptase, HIV protease, and HIV integrase. However, HIV typically undergoes active mutations as it multiplies and renders the virus resistant to the inhibitors administered to patients. Combination therapy, generally referred to as HAART (highly active anti-retroviral therapy), has been developed in which a combination of different anti-HIV inhibitors is administered to a patient. However, viral resistance to combination therapies still frequently develops.

Therefore, although limited success for controlling HIV infection and AIDS has been achieved with previously developed anti-HIV compounds, there is a need for alternative therapeutic approaches that overcome the shortcomings of currently available drugs.

SUMMARY OF THE INVENTION

It has been discovered by the present inventors that the interaction between HIV Gag and PI(4,5)P$_2$ causes a structural change in not only PI(4,5)P$_2$ but also the Gag MA domain protein thereby causing sufficient binding to the plasma membrane to initiate assembly of virus particles. Thus, the complexes formed by the MA domain and PI(4,5)P$_2$, as well as the MA domain and PI(4,5)P$_2$ individually can be used in screening assays to select compounds exhibiting the ability to modulate the interaction between HIV Gag and PI(4,5)P$_2$.

PI(4,5)P$_2$ contains two long-chain fatty acids, typically the fatty acids include stearate and arachidonate at the 1'- and 2'-positions, respectively of the glycerol group, wherein both chains are retained in the lipid bilayer of the plasma membrane. It has been discovered that at least one of the long-chain fatty acids alters its position upon binding to the MA domain thereby stabilizing binding to the MA domain. Specifically, the arachidonate extrudes from the lipid membrane and is sequestered by MA thereby stabilizing association with the plasma membrane, and this stabilization is further enhanced by the extension of myristic acid that was previously sequestered in the MA into the lipid bilayer.

Thus, in one aspect, the present invention relates to a testing method comprising:

(a) contacting a test compound with $PI(4,5)P_2$ or a fragment thereof;

(b) determining the ability of the test compound to bind to the $PI(4,5)P_2$ and exhibiting at least one of the following functions including (1) preventing or reducing binding of the MA domain to the $PI(4,5)P_2$ or a fragment thereof; (2) inhibiting extension of the myristic acid into the lipid bilayer and/or (3) inhibiting the extension of a fatty acid component of PI $(4,5)P_2$ into the MA domain; and (c) evaluating the antiviral effect of the test compound.

In addition, the antiviral effect includes, but is not limited to, inhibition of the formation of a complex that serves as a nucleation site for additional Gag molecules that bind to the membrane in a PI $(4,5)P_2$ independent manner.

In another aspect the present invention relates to a testing method comprising:

(a) contacting a test compound with HIV-1 MA domain of Gag or a fragment thereof;

(b) determining the ability of the test compound to bind to a cavity within the MA domain that is flanked by residues His-89 and Glu-12 and exhibiting at least one of the following functions including (1) inhibiting the formation of a binding interaction between His-89 and Glu-12 residues thereby inhibiting the exposure of a myristyl group of MA or the stabilization of any exposed myristyl group; (2) inhibiting extension of the myristyl group into the lipid bilayer and/or (3) inhibiting a fatty acid component of PI $(4,5)P_2$ from extending into the MA domain; and (c) evaluating the antiviral effect of the test compound.

In yet another aspect, the present invention provides for screening methods for selecting agents for inhibiting the formation of a complex formed between the MA domain of Gag or fragments thereof and $PI(4,5)P_2$ or fragments thereof. The compounds identified in the screening methods of the present invention can be used in studying the interaction between MA and $PI(4,5)P_2$ and further understanding the mechanism of HIV viral propagation. The selected compounds may also be useful in preventing or ameliorating diseases or disorders such as viral infection, particularly HIV infection and AIDS.

Thus, test compounds may be screened in an in vitro binding assay to select compounds capable of interfering with complex formation between the MA domain or fragments thereof and $PI(4,5)P_2$ or fragments thereof and inhibiting the extension of the myristic acid moiety into the lipid bilayer and/or inhibit the extension of a fatty acid chain from the $PI(4,5)P_2$ into the MA domain. In addition, in vitro dissociation assays may also be employed to select compounds capable of dissociating the complexes identified in accordance with the present invention, wherein the MA domain or $PI(4,5)P_2$ has greater affinity for the test compound than each other.

In another aspect, the present invention provides for a screening method that includes the steps of contacting the MA domain or a fragment thereof with $PI(4,5)P_2$ in the presence of one or more test compounds, and detecting the interaction between said the components. Preferably, at least one of the components has a detectable tag. The methods can be conducted in a substantially cell free environment or in a host cell, wherein the host cell includes a lipid bilayer including the $PI(4,5)P_2$ molecule positioned therein. In yet another aspect, the present invention provides for a screening method that comprises at least two components and a testing agent, the method comprising:

(a) providing in a host cell a first component comprising a $PI(4,5)P_2$ molecule positioned within a lipid layer and a second component comprising the Gag MA domain protein or a fragment thereof, wherein the Gag protein has been previously introduced into the cell via an expression vector for expression within the host cell;

(b) providing in said host cell a reporter tag, wherein the reporter tag is triggered by the interaction between $PI(4,5)P_2$ molecule and the MA domain;

(c) allowing said $PI(4,5)P_2$ molecule and MA domain to interact with each other within said host cell in the presence of a test compound; and (d) determining the presence or absence of a triggering of the reporter tag, wherein reduction in triggering of the reporter tag provides for an inhibitory testing agent. In a still further aspect, the present invention provides for a method for determining a compound capable of interfering with the interaction between the MA domain and $PI(4,5)P_2$ which comprises the steps of providing atomic coordinates defining a three-dimensional structure of formed complex, and designing or selecting compounds capable of interfering with the interaction between said MA and $PI(4,5)P_2$ based on changes in said atomic coordinates.

In another aspect, the present invention provides for methods for modulating, in mammalian cells, the interaction of $PI(4,5)P_2$ and a retroviral GAG containing a MA domain sequence from either HIV-1 or HIV-2. The methods can be used to inhibit viral budding, particularly HIV viral budding from infected host cells. Inhibition of viral budding prevents the viruses from being released from the infected host cells thereby suppressing further viral propagation. Accordingly, the present invention also encompasses methods of treating viral infection, particularly HIV infection, and methods of treating and preventing AIDS in patients.

In yet another aspect, the present invention provides for an antibody selectively immunoreactive with a complex formed by the interaction of the Gag MA domain and the $PI(4,5)P_2$ molecule that is administered to cells in vitro or in human bodies to inhibit the activities of the formed complex and/or reduce the concentration of the complex in the cells or patient.

Another aspect of the present invention relates to a method of reducing HIV virus load in an individual. The method generally involves administering to the individual an effective amount of an agent that reduces binding of Gag MA domain to $PI(4,5)P_2$ in a HIV-infected cell of the individual, thereby reducing the level of replication of the virus in the infected cell and the viral load in the individual. The present invention provides a method for treating HIV infection that is distinct from the therapeutic approaches heretofore known the in the art. The method is targeted at a cellular component of the host cells as well as its interaction with a viral protein. The interaction is required for HIV budding from the infected host cells. Accordingly, it is less likely that HIV will develop viral resistance to the treatment according to the present invention.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

During the late phase of HIV type 1 (HIV-1) replication, newly synthesized retroviral Gag proteins are targeted to the plasma membrane of most hematopoietic cell types, where they colocalize at lipid rafts and assemble into immature virions. Membrane binding is mediated by the matrix (MA) domain of Gag, a 132-residue polypeptide containing an N-terminal myristyl group that can adopt sequestered and exposed conformations. Although exposure of the myristyl group is known to promote membrane binding, phosphatidylinositol (PI)4,5-bisphosphate [PI(4,5)$P_2$], a factor that regulates localization of cellular proteins to the plasma membrane, also regulates Gag localization and assembly.

It is shown herein that PI(4,5)$P_2$ binds directly to HIV-1 MA, inducing a conformational change that triggers myristate exposure. Related phosphatidylinositides PI, PI(3)P, PI(4)P, PI(5)P, and PI(3,5)$P_2$ do not bind MA with significant affinity to trigger myristate exposure. Structural studies, described herein, reveal that PI(4,5)$P_2$ adopts an "extended lipid" conformation, in which the inositol head group and 2'-fatty acid chain bind to a hydrophobic cleft in the MA domain, and the 1'-fatty acid and exposed myristyl group bracket a conserved basic surface patch previously implicated in membrane binding. The present findings indicate that PI(4,5)$P_2$ acts as both a trigger of the myristyl switch and a membrane anchor and suggest a potential mechanism for targeting Gag to membrane rafts.

The present invention provides methods of identifying compounds that induce loss of HIV replication in a eukaryotic cell. The methods generally comprise contacting a cell that expresses a Gag protein, and specifically the MA domain, with a testing agent and determining the effect, if any, on the activity of the Gag protein. An agent that induces loss of Gag assembly on the plasma membrane of the cell is a candidate agent for treating HIV-1 or HIV-2.

Figure 13:
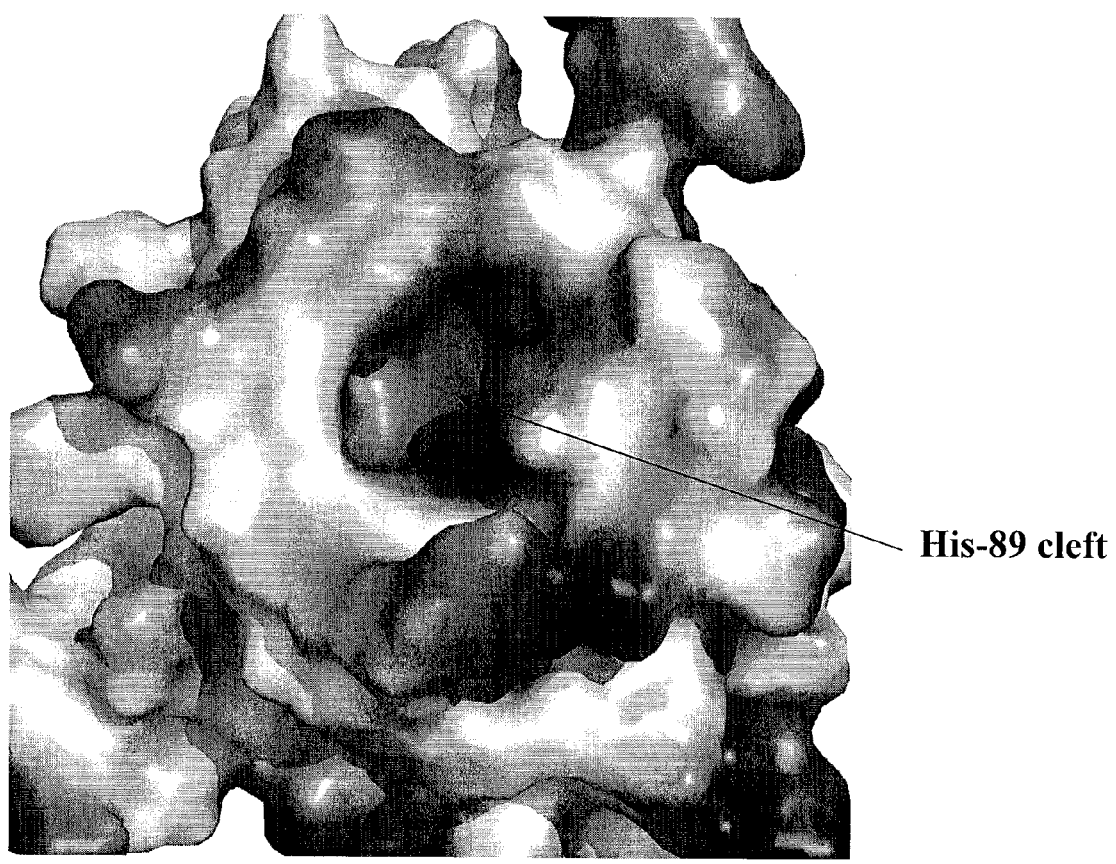
FIG. 13 shows a surface rendering of the myr-sequestered form of the MA domain protein showing the "His-89 cleft" (center) wherein H89 and E12 flank the cavity and subsequently move to form a salt bridge when the myristyl group is exposed.
Figure 14:
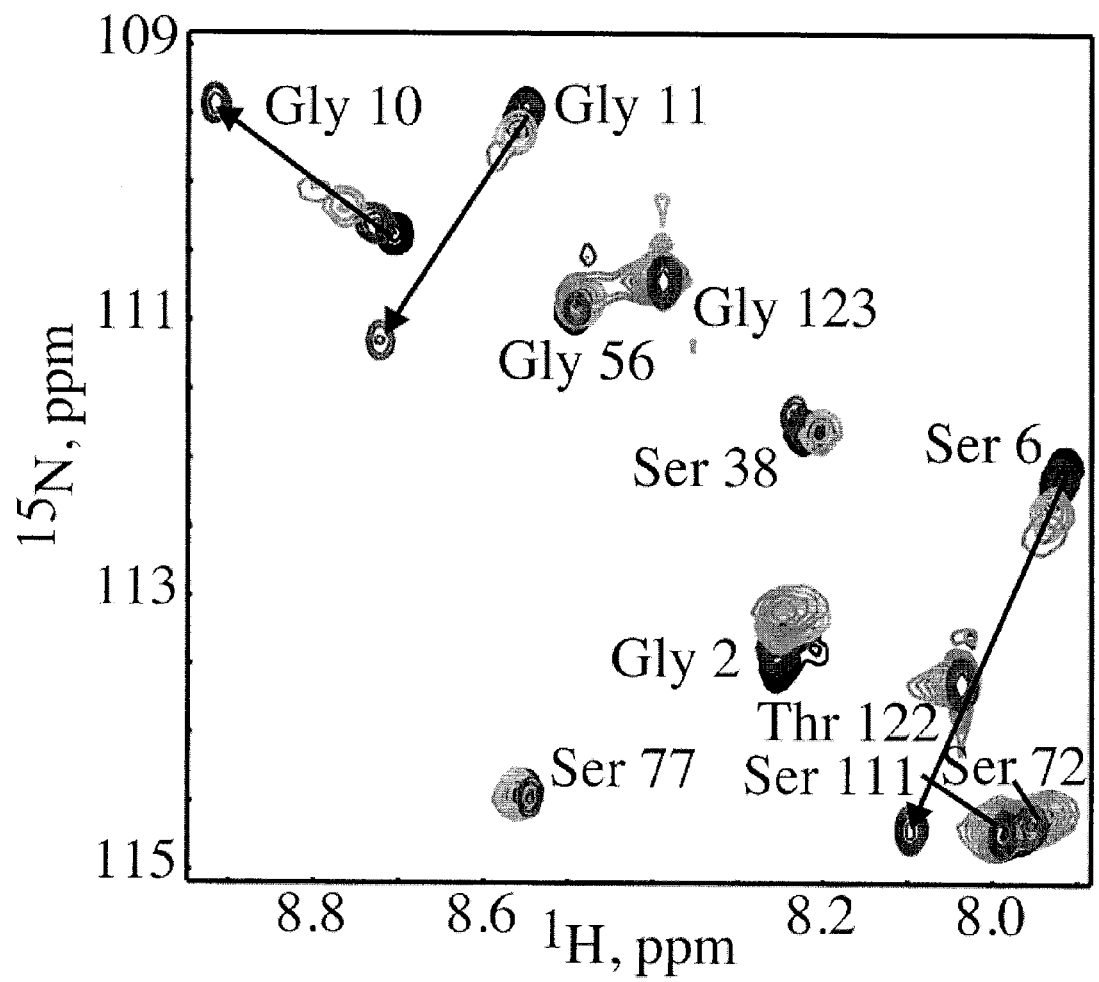
FIG. 14 shows changes in "H-"$^5$N HSQC NMR signals of Helix 1, of FIG. 6, associated with myr exposure and target region for "myristyl switch inhibitors" to inhibit myristate exposure.

The assay can be designed in a number of ways. In one embodiment, the assay provides for determining the effect of a test agent on the activity of $PI(4,5)P_2$ and specifically, changes in the structural conformation of at least one fatty acid of the $PI(4,5)P_2$ wherein inhibition of the extension of such fatty acid into the MA domain reduces binding of Gag to the plasma membrane. In another embodiment, the assay provides for determining the effect of a test agent on the His-89 cleft of the MA domain, as shown in FIG. 13, and the ability to inhibit the exposure of the myristic group and subsequent binding to the plasma membrane. In general, a test agent of interest is one that both inhibits MA domain—$PI(4,5)P_2$ binding and virus assembly on the plasma membrane. A test agent that is active in one assay is typically tested in a second assay method of the invention to provide a test of its specificity.

The terms "candidate agent," "agent", "substance," "test agent," and "compound" are used interchangeably herein. Candidate agents encompass numerous chemical classes, and are generally synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with the MA domain, the PI(4,5)P2 or the complex formed by the binding of the MA domain with the PI(4,5)P2, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A candidate agent is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity are considered candidate agents.

An effective agent has been found to exhibit at least one of the following functions including (1) preventing or reducing binding of the MA domain to the $PI(4,5)P_2$ or a fragment thereof; (2) inhibiting extension of the myristic acid into the lipid bilayer; (3) inhibiting the extension of a fatty acid component of $PI(4,5)P_2$ into the MA domain; and/or (4) inhibiting the formation of a binding interaction between His-89 and Glu-12 residues thereby inhibiting the exposure of a myristyl group of MA or the stabilization of any exposed myristyl group.

Assays of the invention usually include one or more controls. Thus, a test sample includes a test agent, and a control sample has all the components of the test sample except for the test agent.

A variety of reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as nuclease inhibitors, anti-microbial agents, etc. may be used. The components may be added in any order. Incubations are performed at any suitable temperature, typically between 4° C. and 40° C. Incubation periods are selected for optimum activity, but may also be optimized to facilitate rapid high-throughput screening. Typically between 0.1 and 2 hours should be sufficient.

The cells used in the assay are eukaryotic cells, usually mammalian cells, including, but not limited to, primate cells, and including human cells and cell lines. The cells may be primary cell cultures or may be immortalized cell lines. Any eukaryotic cell can be used as long as the cells include a plasma membrane with inclusion of $PI(4,5)P_2$ and wherein the Gag protein can be expressed in the cell. Exemplary cells include human $CD4^+$ T cell lines such as Jurkat, A3.01, H9, and the like; CHO cells; 293 cells; and the like.

In many embodiments, a construct that includes a nucleotide sequence that encodes at least the MA domain of Gag or a fragment thereof, is introduced into the cells, such that the cells are transiently or stably genetically modified with the construct.

Cells can be genetically transformed (genetically modified) with a Gag MA-encoding construct that is a viral construct; a plasmid; a YAC; and the like. Any of a variety of viral vectors can be used, including, but not limited to, adenoviral vectors, adenoassociated viral vectors, vaccinia virus vectors, retroviral vectors, baculoviral vectors, and the like. Plasmids that provide for expression in eukaryotic cells are well known in the art, and many are commercially available.

Any nucleic acid vector having a eukaryotic promoter operably linked to a nucleotide sequence encoding at least the Gag MA domain can be used in the invention to genetically transform a eukaryotic cell. The vectors containing the nucleic acid sequence which may be used in accordance with the invention may be any eukaryotic expression vector.

Techniques for production of nucleic acid constructs for expression of exogenous DNA or RNA sequences in a host are known in the art (see, Sambrook et al. Molecular Cloning: A Laboratory Manual, 2nd Ed., 1989, Cold Spring Harbor Laboratory Press, Cold Spring Harbor, N.Y.)

Various vectors (e.g., vectors capable of replication in eukaryotic hosts) can be used. Numerous vectors which can replicate in eukaryotic hosts are known in the art and are commercially available. In general, such vectors used in accordance with the invention include a eukaryotic promoter operably linked to the Gag MA-encoding nucleotide sequence.

Generally, the DNA construct contains a promoter to facilitate expression of the Gag MA-encoding DNA. The promoter can be a strong, eukaryotic promoter. Exemplary, non-limiting eukaryotic promoters for facilitating transcription in a eukaryotic cell include promoters from cytomegalovirus (CMV), mouse mammary tumor virus (MMTV), Rous sarcoma virus (RSV), and adenovirus early promoter. The promoter can also be an inducible promoter, e.g., a tet-inducible promoter, and the like.

For eukaryotic expression, the construct generally comprises at least a eukaryotic promoter operably linked to the Gag MA-encoding sequence, which is in turn operably linked to a polyadenylation sequence. The polyadenylation signal sequence may be selected from any of a variety of polyadenylation signal sequences known in the art. Preferably, the polyadenylation signal sequence is the SV40 late polyadenylation signal sequence. The construct may also include sequences in addition to promoters which enhance expression in the cell (e.g., enhancer sequences, introns). For example, the construct can include one or more introns, which can increase levels of expression of the Gag MA-encoding nucleotide sequence. Any of a variety of introns known in the art may be used.

Other components such as a marker (e.g., an antibiotic resistance gene (such as an ampicillin resistance gene) or β-galactosidase) to aid in selection of cells containing and/or expressing the construct (e.g., during the process of vector construction), an origin of replication for stable replication of the construct in a bacterial cell (e.g., a high copy number origin of replication, for propagating the vector in a bacterial cell), a nuclear localization signal; a marker that provides for selection in eukaryotic cells (e.g., hygromycin resistance, resistance to mycophenolic acid, and the like); or other elements which facilitate production of the construct, the Gag MA-protein encoded thereby, or both.

Methods of genetically transforming a eukaryotic cell are well known to those skilled in the art and include, but are not limited to, electroporation, lipofection, infection, use of cationic lipids, use of dextran sulfate, and the like.

The invention further provides methods of identifying compounds that inhibit activity of Gag to the PM for virus assembly. The methods generally comprise contacting the Gag MA domain or $PI(4,5)P_2$ with a test agent, and determining the effect, if any on the virus assembly. An agent that inhibits such virus assembly is a candidate agent for treating HIV-1 or HIV-2. Specifically, an agent of interest will exhibit at least one of the following functions including; inhibiting at least one of the fatty acids of $PI(4,5)P_2$ from extending into a hydrophobic region of the MA domain; inhibiting the myristyl group from extending into the plasma membrane upon co-location with $PI(4,5)P_2$; and/or binding to a cavity in the MA domain flanked by His-89 and Glu-12 and inhibiting exposure of the myristyl group by blocking such site.

Detectable tags used as reporter tags, may include, but are not limited to, tags that are capable of being assayed, generally quantitatively, by radiolabels, by photochemical, colorimetric, chromogenic, fluorescent, fluorogenic, phosphorescent, electrochemical, chemiluminescent or bioluminescent or immunoassays. Exemplary tags are those detectable in colorimetric, chromogenic, fluorescent, fluorogenic, chemiluminescent or bioluminescent assays. Further exemplary tags are those that include a tag group that can be a radioactively tagged group, or a fluorogenic tag, a chromogenic tag or a chemiluminescent tag.

In general, a test agent is prepared in a pharmaceutically acceptable composition for delivery to a host. Pharmaceutically acceptable carriers preferred for use with a test agent may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a test agent may also be lyophilized using means well known in the art, for subsequent reconstitution and use according to the invention.

In general, the pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. Preservatives and other additives may also be present such as, for example, antimicrobials, antioxidants, chelating agents, and inert gases and the like. In one embodiment, a subject agent formulation comprises additional anti-mycobacterial and/or anti-bacterial agent(s).

A test agent can be administered in the absence of agents or compounds that might facilitate uptake by target cells. In the alternative, a subject agent can be administered with compounds that facilitate uptake of a subject agent by target cells (e.g., by macrophages) or otherwise enhance transport of a subject agent to a treatment site for action. Absorption promoters, detergents and chemical irritants (e.g., keratinolytic agents) can enhance transmission of a subject agent into a target tissue (e.g., through the skin).

A colloidal dispersion system may be used for targeted delivery of the test agent to specific tissue. Colloidal dispersion systems include macromolecule complexes, nanocapsules, microspheres, beads, and lipid-based systems including oil-in-water emulsions, micelles, mixed micelles, and liposomes.

Method of Treating HIV Infection

The present invention provides methods of treating a HIV infection in an individual. The methods generally involve administering to an individual having a HIV infection an agent in an amount effective to reduce replication of HIV in the individual, thereby treating the infection.

A therapeutically effective amount of an effective agent that reduces virus assembly in a HIV infected cell is an amount that reduces the level or replication in the individual by at least about 10%, at least about 20%, at least about 30%, at least about 40%, at least about 50%, at least about 60%, at least about 70%, at least about 80%, at least about 90%, or at least about 95% or more, compared to the levels of the individual not treated with the agent.

Treating a HIV infection, includes, but is not limited to, preventing HIV infection, reducing the probability of HIV infection, reducing the spread of HIV from an infected cell to a susceptible cell, reducing viral load in an HIV-infected individual, reducing an amount of virally-encoded polypeptide(s) in an HIV-infected individual, and increasing CD4 T cell count in an HIV infected individual.

The amount of an effective agent which is administered will vary with the nature of the drug. As one non-limiting example, a subject agent can be administered in the range of about 0.2 to 20 mg/kg/day. The determination of how large a dosage to be used may be determined using the small animal model and relating the dosage based on pharmacokinetics, e.g. with equations predictive of interspecies scaling. Usually, the lowest effective dose will be used.

An effective agent is administered to an individual using any available method and route suitable for drug delivery. Conventional and pharmaceutically acceptable routes of administration include intranasal, intramuscular, intratracheal, intratumoral, subcutaneous, intradermal, topical application, intravenous, vaginal, rectal, nasal, oral and other parenteral routes of administration. Routes of administration may be combined, if desired, or adjusted depending upon the subject agent and/or the desired effect on the immune response. The effective agent can be administered in a single dose or in multiple doses, and may encompass administration of booster doses, to maintain the desired effect.

An effective agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Inhalational routes of administration (e.g., intranasal, intrapulmonary, and the like) are particularly useful in stimulating an immune response for prevention or treatment of infections of the respiratory tract. Such means include inhalation of aerosol suspensions or insufflation of the polynucleotide compositions of the invention. Nebulizer devices, metered dose inhalers, and the like suitable for delivery of polynucleotide compositions to the nasal mucosa, trachea and bronchioli are well-known in the art and will therefore not be described in detail here.

Parenteral routes of administration other than inhalation administration include, but are not necessarily limited to, topical, transdermal, subcutaneous, intramuscular, intraorbital, intraspinal, intrasternal, and intravenous routes, i.e., any route of administration other than through the alimentary canal. Parenteral administration can be carried to effect systemic or local delivery of subject agent.

Systemic administration typically involves intravenous, intradermal, subcutaneous, or intramuscular administration or systemically absorbed topical or mucosal administration of pharmaceutical preparations. Mucosal administration includes administration to the respiratory tissue, e.g., by inhalation, nasal drops, ocular drop, etc.; anal or vaginal routes of administration, e.g., by suppositories; and the like. An effective agent can also be delivered to the subject by enteral administration. Enteral routes of administration include, but are not necessarily limited to, oral and rectal (e.g., using a suppository) delivery.

Any of a variety of methods can be used to determine whether a treatment method is effective. For example, methods of determining whether the methods of the invention are effective in reducing HIV entry into a cell, and/or treating an HIV infection, are any known test for indicia of HIV infection, including, but not limited to, measuring viral load, e.g., by measuring the amount of HIV in a biological sample, e.g., using a polymerase chain reaction (PCR) with primers specific for a HIV polynucleotide sequence; detecting and/or measuring a polypeptide encoded by HIV, e.g., p24, gp120, reverse transcriptase, using, e.g., an immunological assay with an antibody specific for the polypeptide; and measuring CD4 cell count in the individual. Methods of assaying an HIV infection (or any indicia associated with an HIV infection) are known in the art, and have been described in numerous publications such as HIV Protocols (Methods in Molecular Medicine, 17) N. L. Michael and J. H. Kim, eds. (1999) Humana Press.

An effective agent can be administered to an individual in combination (e.g., in the same formulation or in separate formulations) with another therapeutic agent ("combination therapy"). The effective agent can be administered in admixture with another therapeutic agent or can be administered in a separate formulation. When administered in separate formulations, a subject agent and another therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more.

Therapeutic agents that can be administered in combination therapy, such as anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat antiviral infections. In some embodiments, patients with a viral or bacterial infection are treated with a combination of one or more subject agents with one or more of the following; beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide®), trisodium phosphonoformate (Foscarnet®), famcyclovir, pencyclovir, valacyclovir, nucleic acid/replication inhibitors, interferon, zidovudine (AZT, Retrovir®), didanosine (dideoxyinosine, ddI, Videx®), stavudine (d4T, Zerit®), zalcitabine (dideoxycytosine, ddC, Hivid®), nevirapine (Viramune®), lamivudine (Epivir®, 3TC), protease inhibitors, saquinavir (Invirase®, Fortovase®), ritonavir (Norvirg), nelfinavir (Viracept®), efavirenz (Sustiva®), abacavir (Ziagen®), amprenavir (Agenerase®) indinavir (Crixivan®), ganciclovir, AzDU, delavirdine (Rescripto®), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

The methods of the present invention are suitable for treating individuals who have an HIV infection; who are at risk of contracting an HIV infection; and who were treated for an HIV infection, but who relapsed. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals; intravenous drug users; individuals who may have been exposed to HIV-infected blood, blood products, or other HIV-contaminated body fluids; babies who are being nursed by HIV-infected mothers. Individuals suitable for treatment include individuals infected with, or at risk of becoming infected with, HIV-1 and/or HIV-2 and/or HIV-3, or any variant thereof.

Individuals suitable for treatment with the methods of the invention also include individuals who have an HIV infection that is refractory to treatment with other antiviral therapies. Individuals suitable for treatment include non infected individuals that have a high risk of HIV exposure and should be protected from establishment of HIV infection following exposure to HIV.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

Sample Preparation

HIV-1 myrMA and myr(−)MA proteins were prepared as described (19, 37). Phosphoinositides $PI(4,5)P_2$, di-$C_4$-PI(4,5)$P_2$, di-$C_8$-PI(4,5)$P_2$, di-$C_4$-PI, di-$C_4$-PI(3)P, di-$C_4$-PI(4)P, di-$C_4$-PI(5)P, di-$C_4$-PI(3,5)$P_2$, di-$C_8$-PI(3,4,5)$P_2$, and di-$C_4$-PI (Echelon, Salt Lake City, Utah) and di-$C_4$-phosphatidylcholine (Avanti Polar Lipids) were obtained commercially and used without further purification. Samples for all NMR experiments were prepared in 50 mM sodium phosphate at pH 5.5 and 5 mM DTT.

NMR Spectroscopy

NMR data [Bruker DRX (Billerica, Mass.); 800 MHz $^1$H and DMX 600 MHz $^1$H spectrometers equipped with cryoprobes] were obtained from a combination of 2D, 3D, and 4D NOESY data, for combinations of natural abundance; $^{15}$N-, $^{15}$N-, and $^{13}$C-labeled protein samples (35° C.). Protein signals were assigned as described (19, 37). Phosphoinositide signals were assigned from 2D heteronuclear multiple-quantum coherence (HMQC), heteronuclear multiple bond correlation (HMBC), NOESY, total correlation spectroscopy (TOCSY), and COSY data (the $^1$H and $^{13}$C NMR signals of the 1'- and 2'-acyl chains were resolved in the 2D spectra), and intra- and intermolecular $^1$H-$^1$H NOEs were assigned from 2D ($^1$H-$^1$H), 3D ($^{13}$C-, $^{15}$N-, and $^{13}$C-edited/$^{12}$C-double-half-filtered), and 4D (5N/$^{13}$C- and $^{13}$C/$^{13}$C-edited) NOESY data (39, 40). Binding isotherms from $^1$H-$^{15}$N NMR HSQC titration experiments were calculated with ORIGIN 7.0 software (Microcal Software, Northampton, Mass.).

Structure Calculations. Upper interproton distance bounds of 2.7, 3.3, and 5.0 Å (with appropriate corrections for pseudoatoms) were used for NOE crosspeaks of strong, medium, and weak intensity, respectively, which were qualitatively determined after intensity normalization of the different NOE data sets. No backbone hydrogen bond or chemical shift-based torsion angle restraints were used. $^1$H-$^{15}$N residual dipolar couplings (RDCs) were measured for myr(s) MA, myr(−)MA, and PI(4,5)$P_2$ complexes with myr(−)MA. Structures of myr(−)MA and myr(s)MA calculated with RDC restraints exhibited improved convergence but were in the range of structures calculated without these restraints. Residual dipolar coupling (RDC) data obtained for myr(−) MA and myr(−)MA:di-$C_4$-PI(4,5)$P_2$ were very similar and, consistent with the NOE data, indicate that PI(4,5)$P_2$ binding does not significantly alter the structure of the β-hairpin or the β-I-V-binding site. RDCs could not be reliably measured for myristate-exposed species due to interactions with the alignment media and the tendency to form trimers (19). To avoid potential biases, comparisons with myr(e)MA were made by using structures calculated without the use of dipolar coupling restraints. Structures were calculated in torsion angle space with CYANA (L.A. Systems, Toshigi, Japan), starting from random initial angles.

Example 1

PI(4,5)$P_2$ Binds HIV-1 MA and Triggers Myristate Exposure

Figure 1:
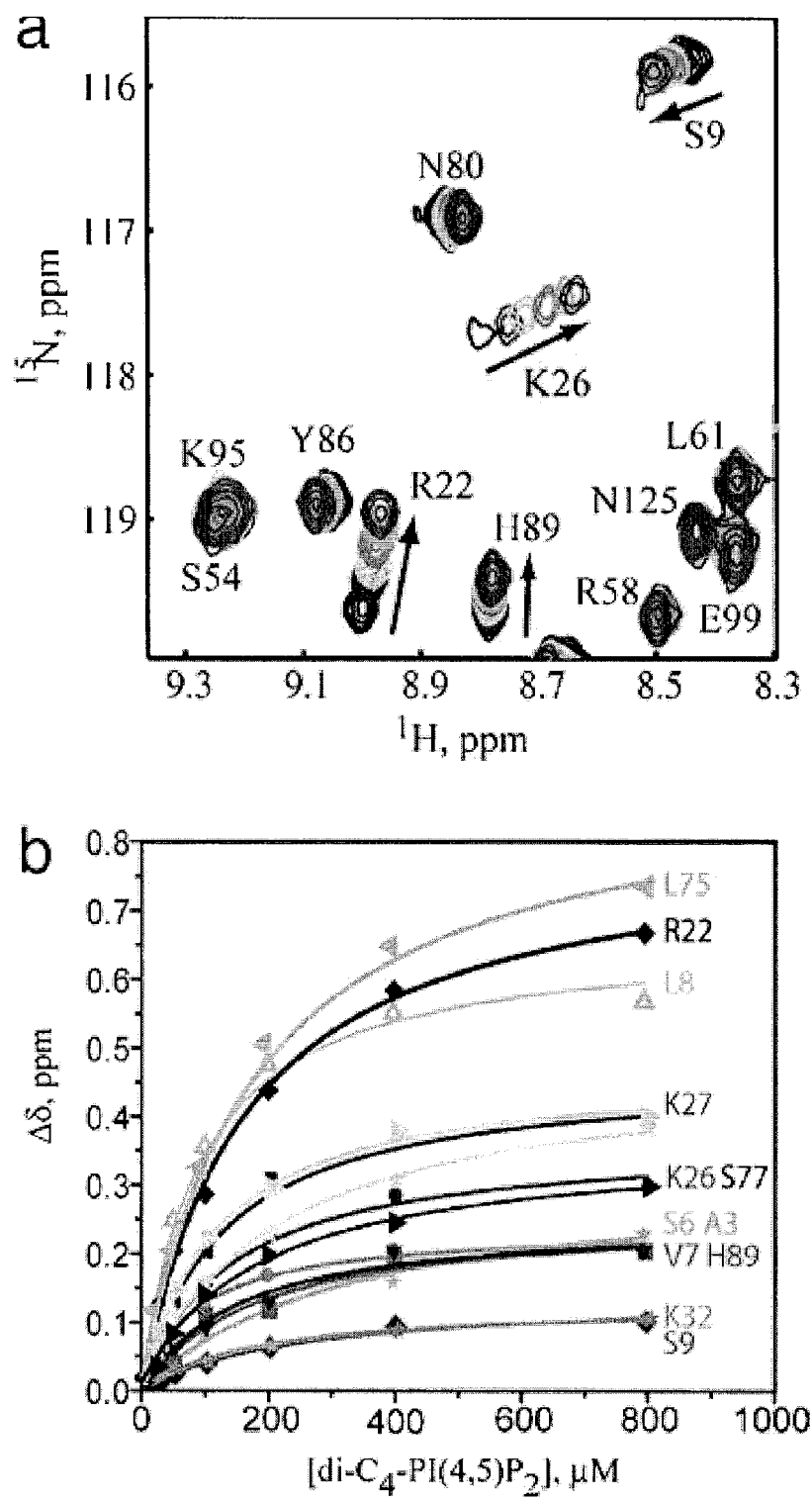
FIG. 1 shows representative NMR data and structure of HIV-1 myrMA bound to di-$C_4$-PI(4,5)$P_2$. (a) Overlay of 2D $^1$H-$^{15}$N HSQC spectra upon titration with di-$C_4$-PI(4,5)$P_2$ [50 µM, 35° C.; di-$C_4$-PI(4,5)$P_2$:MA at different concentrations including 0:1, 1:1, 2:1, 4:1, 8:1, and 16:1], wherein a subset of signals shifted as a function of increasing di-$C_4$-PI(4,5)$P_2$ concentrations indicating site-specific binding; (b) $^{15}$N NMR chemical-shift titration data, which fit to 1:1 binding isotherms ($K_d$=150±30 µM).
Figure 8:
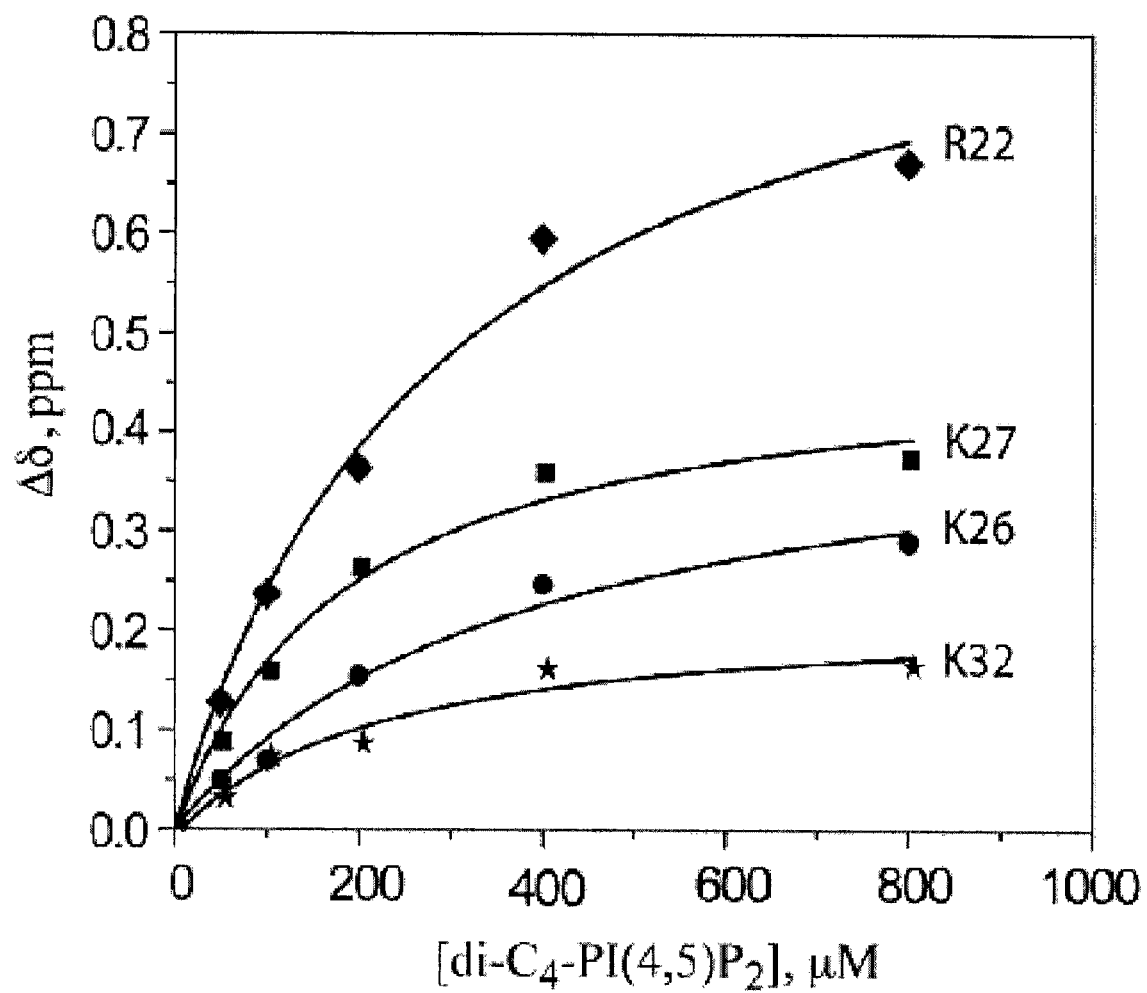
FIG. 8 shows $^{15}$N NMR chemical-shift titration data for di-$C_4$-PI(4,5)$P_2$ binding to HIV-1 myr(−) matrix protein (MA) and nonlinear least-squares fitting to 1:1 binding isotherms ($K_d$=240±60 µM).

To gain insight into the structural basis for PI(4,5)$P_2$-dependent membrane targeting, NMR studies of phosphatidylinositide interactions with the HIV-1 MA protein were conducted. PI phosphates contain two long-chain fatty acids that promote micelle formation in aqueous solution (34). The most abundant cellular form of PI(4,5)$P_2$ contains stearate and arachidonate at the 1'- and 2'-positions of the glycerol group, respectively (35). Addition of substoichiometric amounts of this PI(4,5)$P_2$ species to unmyristoylated [myr(−)]MA and myrMA led to severe broadening in the $^1$H-$^{15}$N heteronuclear single-quantum coherence (HSQC) NMR spectra, and at 1:1 PI(4,5)$P_2$:MA stoichiometries, signals for backbone NH groups were broadened beyond detection. Attempts to study native PI(4,5)$P_2$ binding in the presence of dodecylphosphocholine detergent micelles, which were successfully used to study PI-3-phosphate interactions with the FYVE membrane-binding domain (36), were precluded by detergent-induced protein unfolding. Studies were therefore conducted with soluble forms of PI(4,5)$P_2$ containing truncated lipids. Representative $^1$H-$^{15}$N HSQC NMR data obtained upon titration of myrMA with di-butyryl-PI(4,5)$P_2$ [di-$C_4$-PI(4,5)$P_2$] are shown in FIG. 1(a). Although a majority of the signals were relatively insensitive to titrations, a subset of signals corresponding to residues Arg-22, Lys-26, Lys-27, His-33, Glu-73, Leu-75, and Ser-77 (group 1) exhibited significant chemical-shift changes upon addition of di-$C_4$-PI(4,5)$P_2$ $(\Delta\delta_{HN}((\Delta\delta^1_H)^2+(\Delta\delta^{15}_N)^2)^{1/2})$=0.1-0.8 ppm; see FIG. 1(b). These residues reside on helices II and V and a meandering 1-hairpin and contribute to a hydrophobic cleft (β-II-V cleft; refs. 37 and 38). Nonlinear least-squares fits of the titration data afforded a dissociation constant ($K_d$) of 150±30 μM (mean±SD; FIG. 1(b)). Similar results were obtained upon titration of myr(−)MA with di-$C_4$-PI(4,5)$P_2$ ($K_d$=240±60 M as shown in FIG. 8. Titration of myrMA with di-octyl-PI(4,5)$P_2$ [di-$C_8$-PI(4,5)$P_2$], which contains longer fatty acid chains, resulted in similar chemical-shift changes at low di-$C_8$-PI(4,5)$P_2$:myrMA ratios (<0.5: 1), but aggregation and signal broadening at higher ratios precluded quantitative determination of the binding constant. Signal broadening was not observed upon titration of myr(−) MA with di-$C_8$-PI(4,5)$P_2$, which binds with >3-fold greater affinity than di-$C_4$-PI(4,5)$P_2$ ($K_d$=83±4 μM; see FIG. 9(a).

For the myristoylated MA protein, a second subset of residues (group 2: Gly-2-Ser-9, Glu-12-Asp-15, Arg-39, and His-89) that are well removed from the group 1 residues in the MA protein structure (37, 38) exhibit di-$C_4$-PI(4,5)$P_2$— and di-$C_8$-PI(4,5)$P_2$-dependent "H-"$^5$N HSQC signals that shift progressively toward values observed for myr(−)MA. Similar changes were observed previously for these residues upon concentration-dependent protein trimerization (19) and are indicative of a shift in the myristyl switch equilibrium from a predominantly myr(s) to a myr(e) state. Structural studies (below) confirmed that these spectral changes reflect di-$C_4$-PI(4,5)$P_2$-dependent exposure of the myristyl group.

Example 2

Structure of the di-$C_4$-PI(4,5)$P_2$:myrMA Complex

Figure 2:
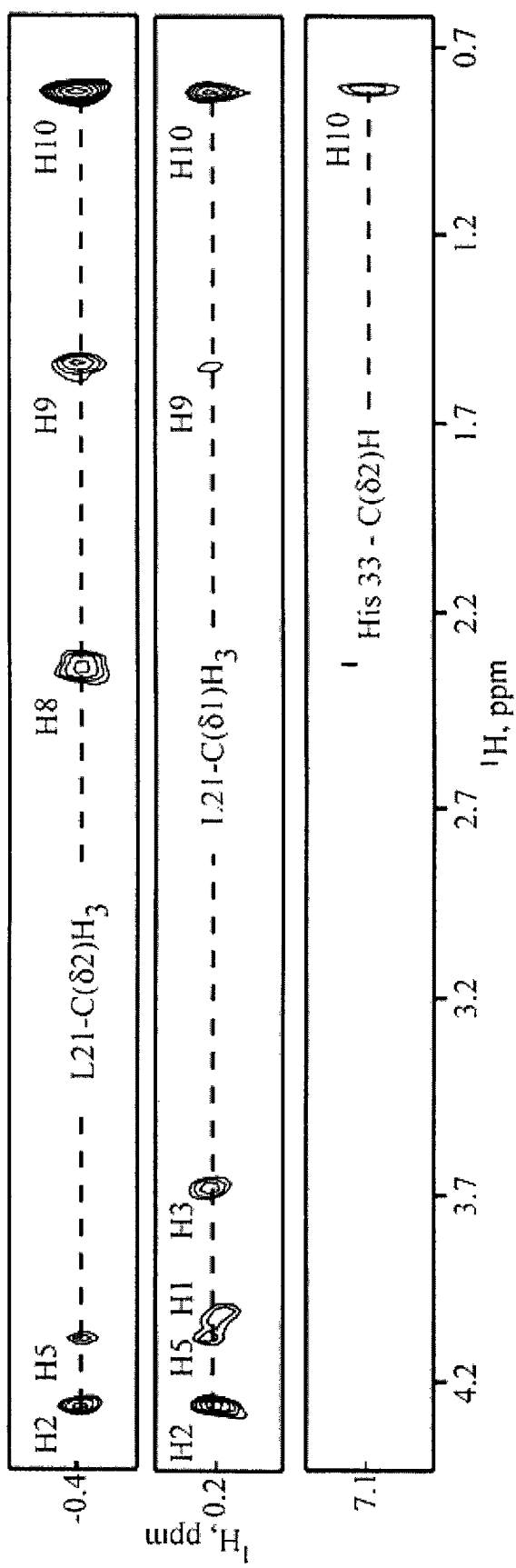
FIG. 2 shows representative $^{13}$C-edited/$^{12}$C-double-half-filtered NOE data showing unambiguously assigned intermolecular NOEs.
Figure 3:
FIG. 3 shows a stereoview showing the best-fit backbone superposition of the 20 refined structures calculated for the myr(e)MA:di-$C_4$-PI(4,5)$P_2$ complex.
Figure 3:

The structure of the di-$C_4$-PI(4,5)$P_2$:myrMA complex was determined by using a combination of $^{15}$N-, $^{13}$C-, $^{15}$N/$^{13}$C-, $^{13}$C/$^{13}$C-, and $^{13}$C-edited/$^{12}$C-double-half-filtered nuclear Overhauser effect (NOE) experiments, as shown in FIG. 2. NOEs observed between the myristyl group and core residues of myr(s)MA were absent in the di-$C_4$-PI(4,5)$P_2$:myrMA complex, confirming that di-$C_4$-PI(4,5)$P_2$ binding causes extrusion of the myristyl group. The NMR data are consistent with a single binding mode, in which the glycerol moiety packs against the side chains of His-33 and Trp-36, and the $C_4$-acyl chain attached to the 2'-position of the glycerol packs within the β-II-V cleft against the side chains of Leu-21, Lys-27, Tyr-29, His-33, Trp-36, and Ser-77. The phosphoinositide head group packs against Leu-21 and Lys-27, burying the 2'-fatty acid chain, as shown in FIG. 3. The 1'-acyl chain does not exhibit NOEs with the protein and appears exposed to solvent and disordered. In addition to the hydrophobic contacts, the 1'-phosphodiester is poised to make favorable electrostatic interactions with the positively charged side chains of His-33 and Lys-27, and the 4'- and 5'-phosphates are positioned to form salt bridges with the side chains of Arg-22 and Arg-76, respectively. No intermolecular interactions were observed for Lys-30 or Lys-32, which were predicted to bind to PI(4,5)$P_2$ on the basis of N-hydroxysuccin (NHS)-biotin protection experiments (32).

Figure 4:
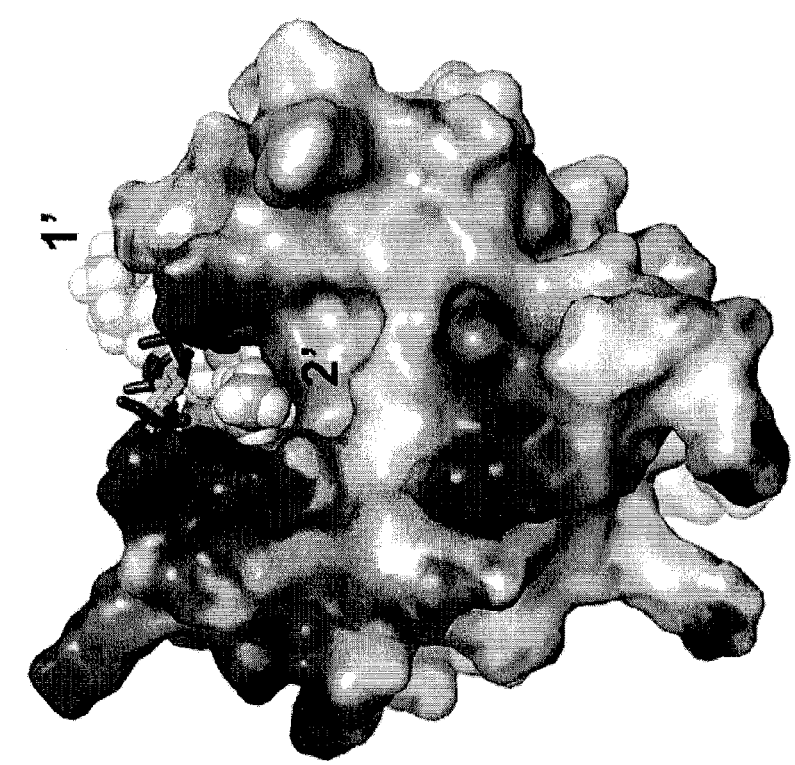
FIG. 4 shows the structure of the di-$C_8$-PI(4,5)$P_2$:myr(−)MA complex. (a) Interactions between di-$C_8$-PI(4,5)$P_2$ (sticks) and myr(−)MA showing the 2'-fatty acid extending in a hydrophobic cleft and the inositol ring packing against a basic patch of the protein. (b) The structure is rotated ≈90° relative to (a), and the $C_8$ acyl chains are shown in space-filling format.
Figure 4:
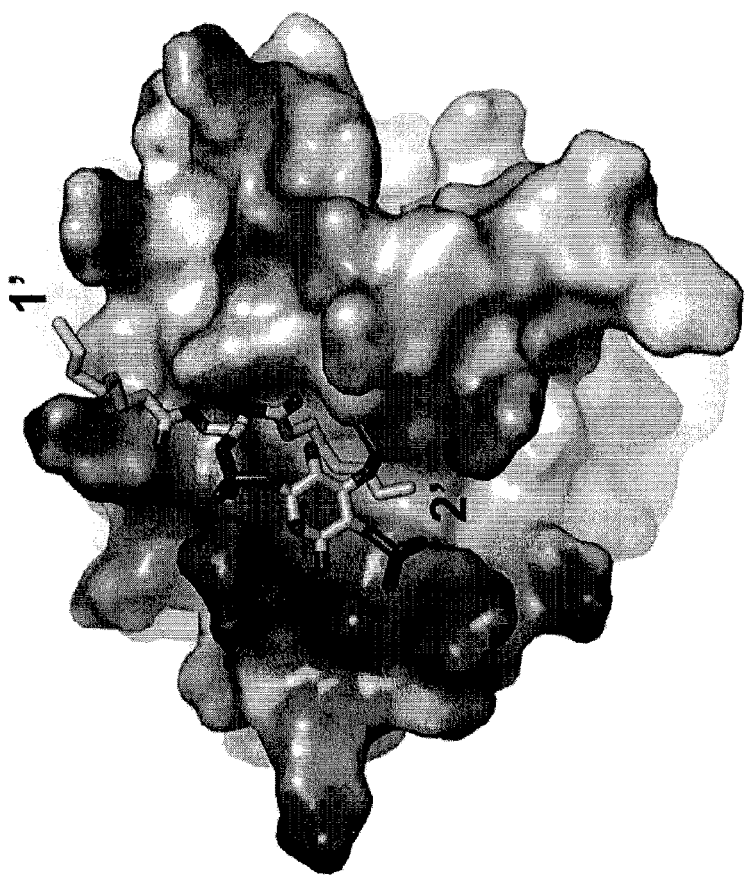
Figure 5:
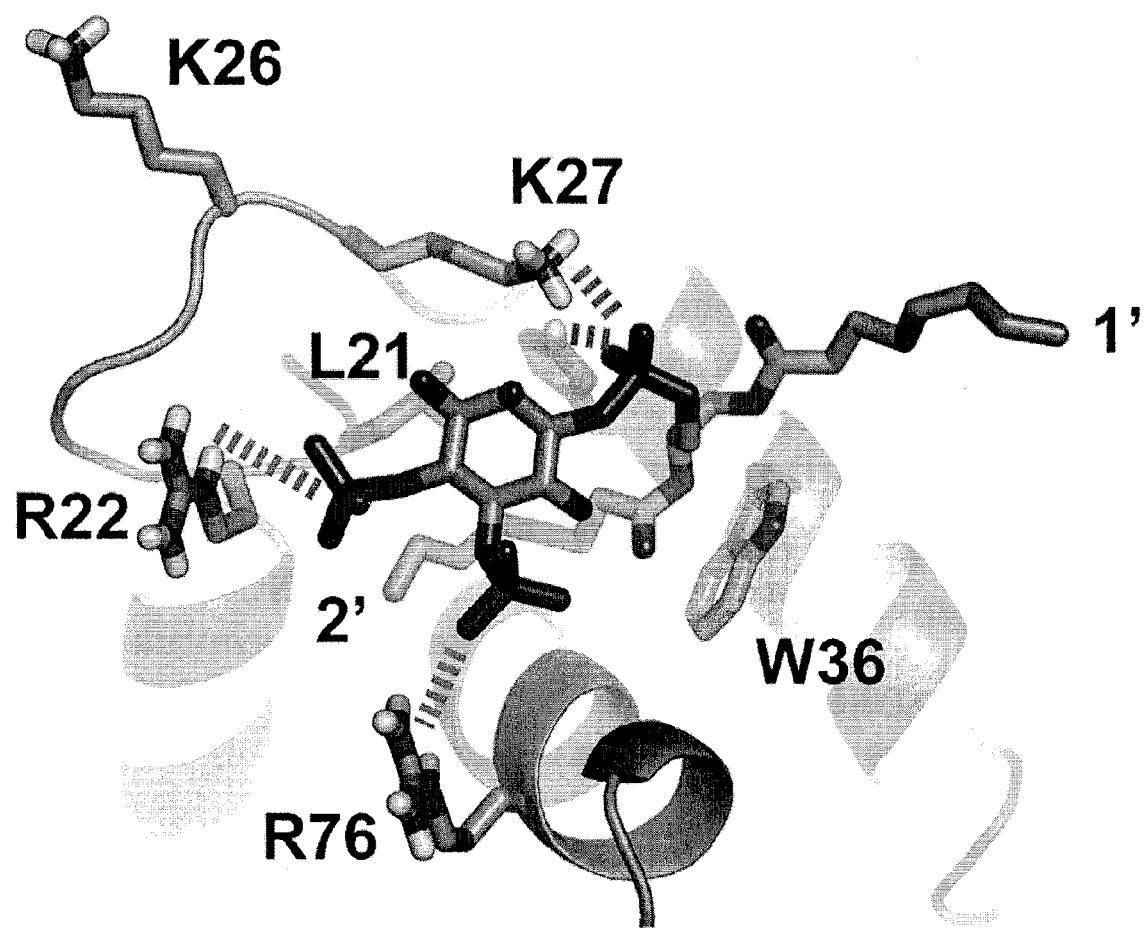
FIG. 5 shows the structure of the di-$C_8$-PI(4,5)$P_2$:myr(−)MA complex showing the electrostatic interactions implicated in binding.
Figure 9:
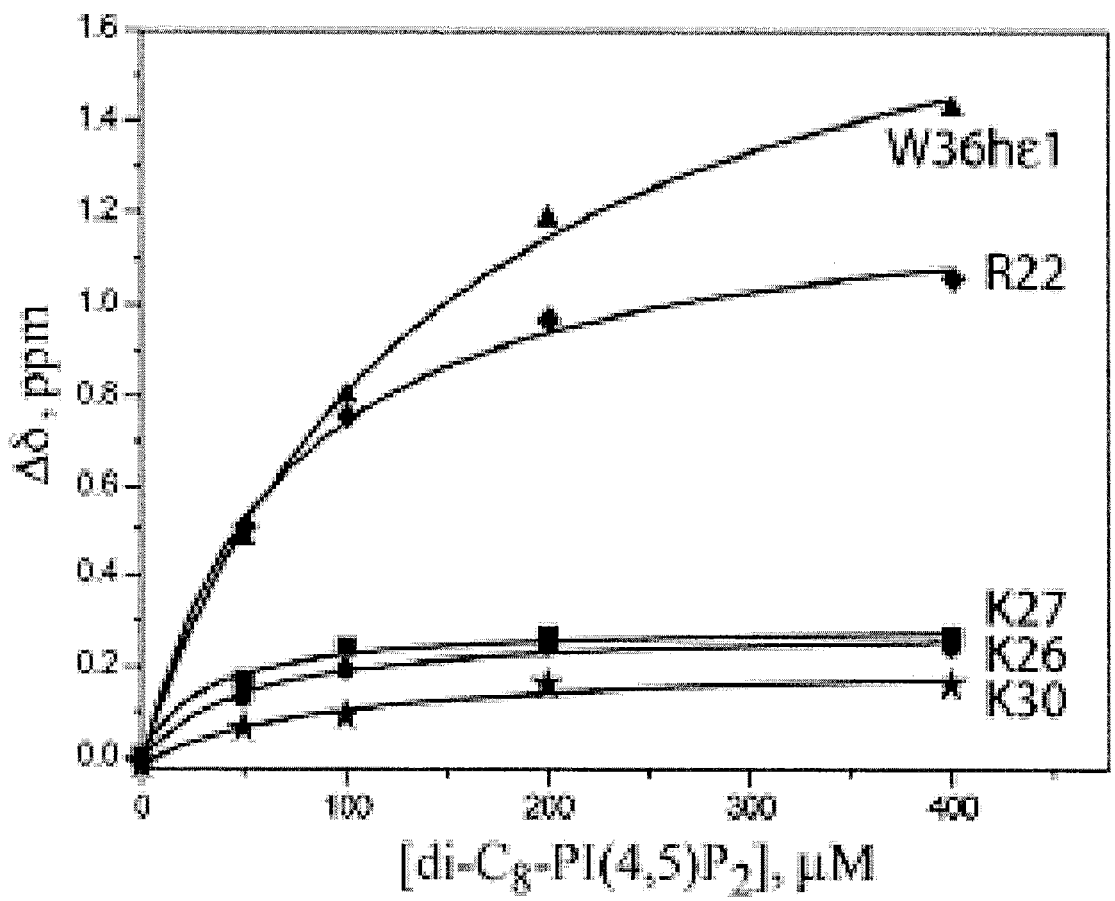
FIG. 9 shows $^{15}$N NMR chemical-shift titration data obtained for di-$C_8$-PI(4,5)$P_2$ binding to HIV-1 myr(−)MA and nonlinear least-squares fitting to 1:1 binding isotherms ($K_d$=83±4 µM).
Figure 10:
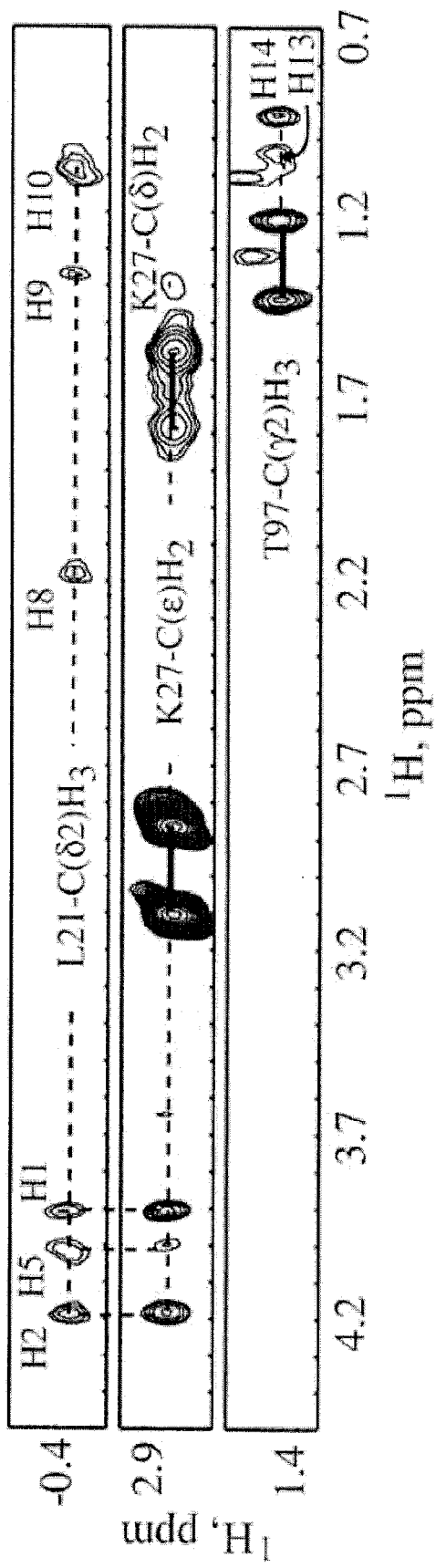
FIG. 10 shows representative $^{13}$C-edited/$^{12}$C-double-half-filtered NOE data showing unambiguously assigned intermolecular NOEs, including those between Thr 97-C(γ2)$H_3$ and the terminal methyl of the 2'-$C_8$ acyl chain. Solid and dashed lines denote $^1$H-$^{12}$C breakthrough doublets and intermolecular NOE peaks, respectively.
Figure 11:
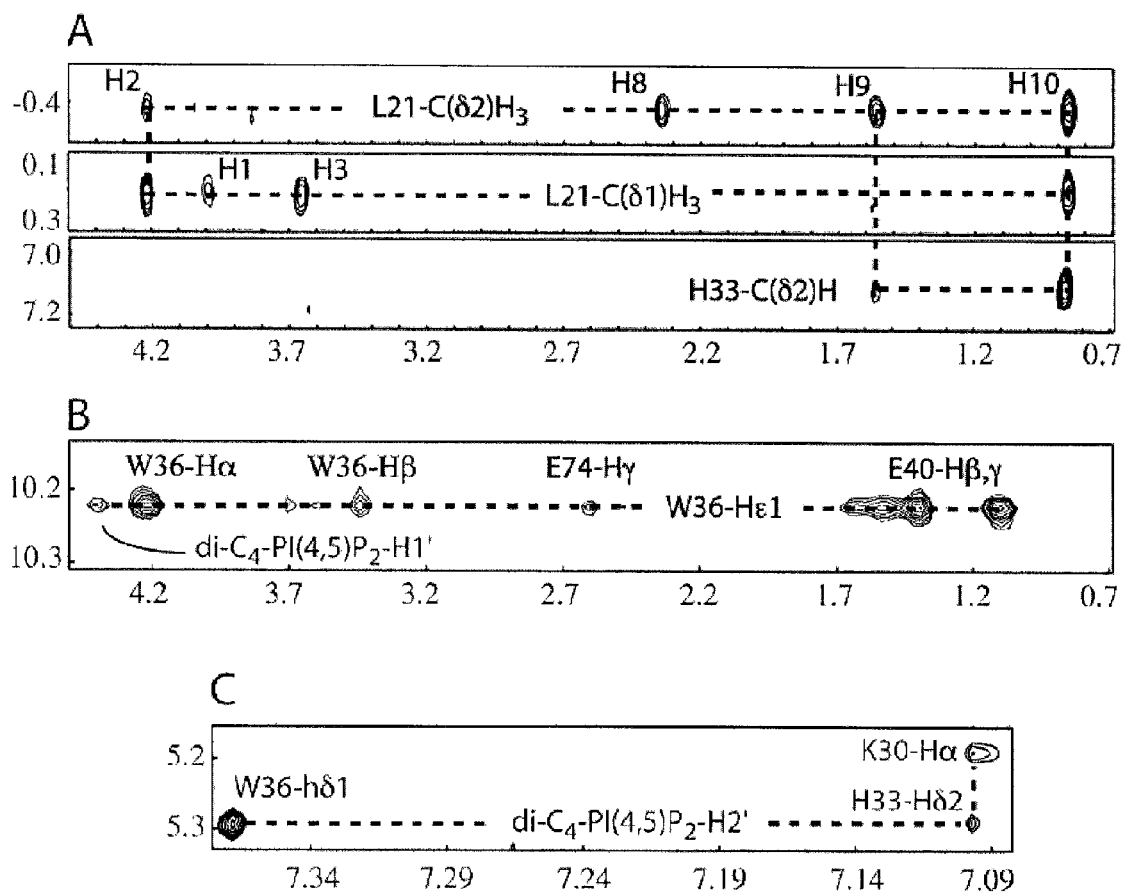
FIG. 11 shows representative NMR data obtained for HIV-1 myr(−)MA bound to di-$C_4$-PI(4,5)$P_2$ showing unambiguously assigned intermolecular NOEs. (a) $^{13}$C-edited/$^{12}$C-double-half-filtered NOE data. (b) $^{15}$N-edited NOE data. (c) 2D NOESY data.
Figure 12:
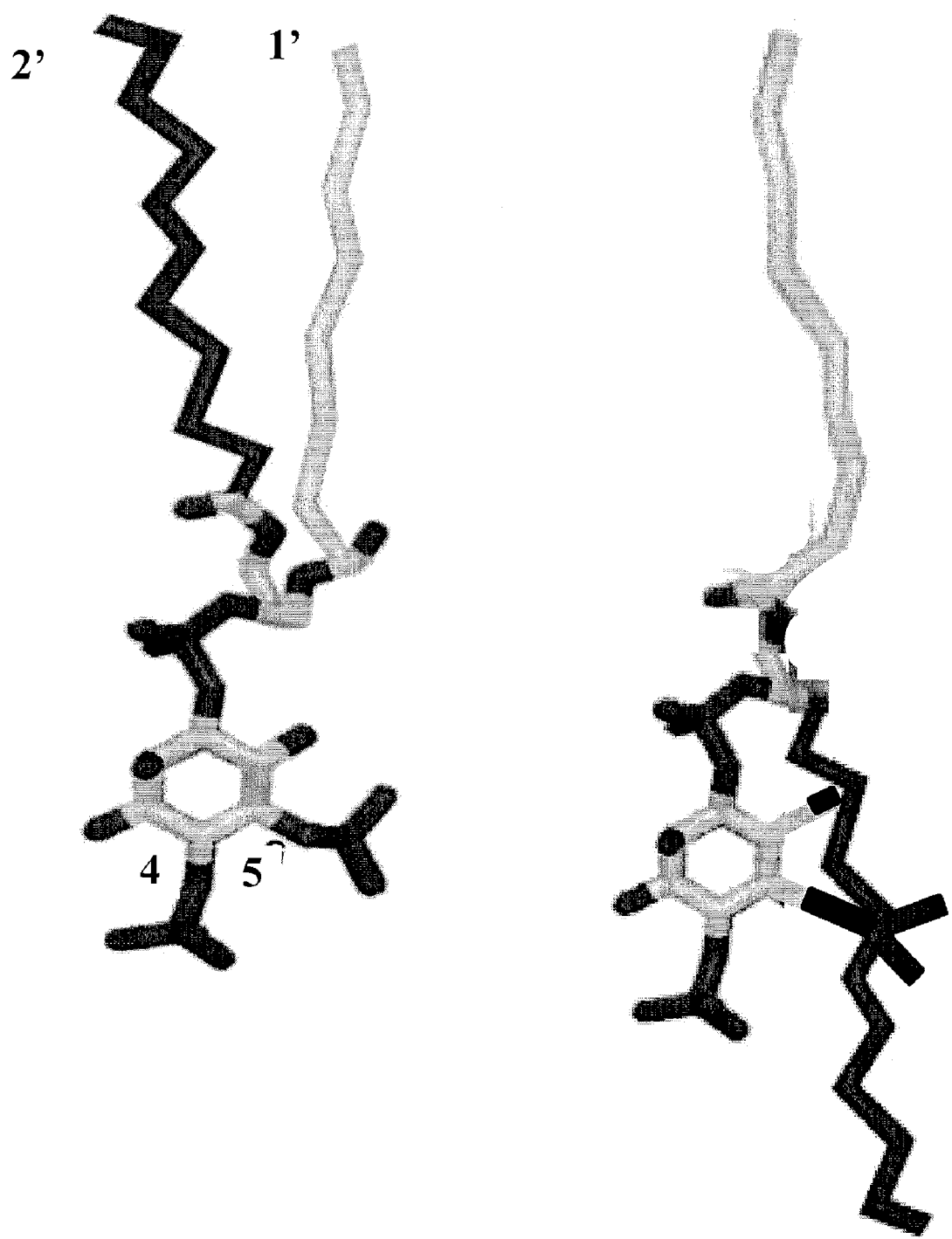
FIG. 12 shows structural changes of PI(4,5)$P_2$ before and after binding to the MA domain and the extension of fatty acid 2' from the lipid bilayer into contact with and sequestering by MA.

To determine whether the N-terminal myristyl group influences the binding mode, we determined the structure of the di-$C_4$-PI(4,5)$P_2$ complex with myr(-)MA. di-$C_4$-PI(4,5)$P_2$ binds myr(-)MA and myrMA in an essentially identical manner, as might be expected given the similar di-$C_4$-PI(4,5)$P_2$-dependent chemical-shift changes and binding constants, as shown in FIG. 11. The structure of the di-$C_8$-PI(4,5)$P_2$ complex with myr(-)MA was determined and this structure is very similar to that observed for di-$C_4$-PI(4,5)$P_2$:myr(-)MA, except that the additional residues of the 2'-fatty acid chain extend further into the β-II-V cleft (FIGS. 4 and 9). The additional hydrophobic contacts appear to be responsible for the 3-fold enhanced affinity of di-$C_8$-PI(4,5)$P_2$ for myr(-)MA relative to di-$C_4$-PI(4,5)$P_2$. As observed in the di-$C_4$-PI(4,5)$P_2$:myrMA structure, the 1'-phosphodiester is poised to interact electrostatically with His-33 and Lys-27, and the 4'- and 5'-phosphates are poised to interact with Arg-22 and Arg-76, respectively, as shown in FIG. 5.

Example 3

Myristate Exposure is Induced by an Allosteric Mechanism

Figure 6:
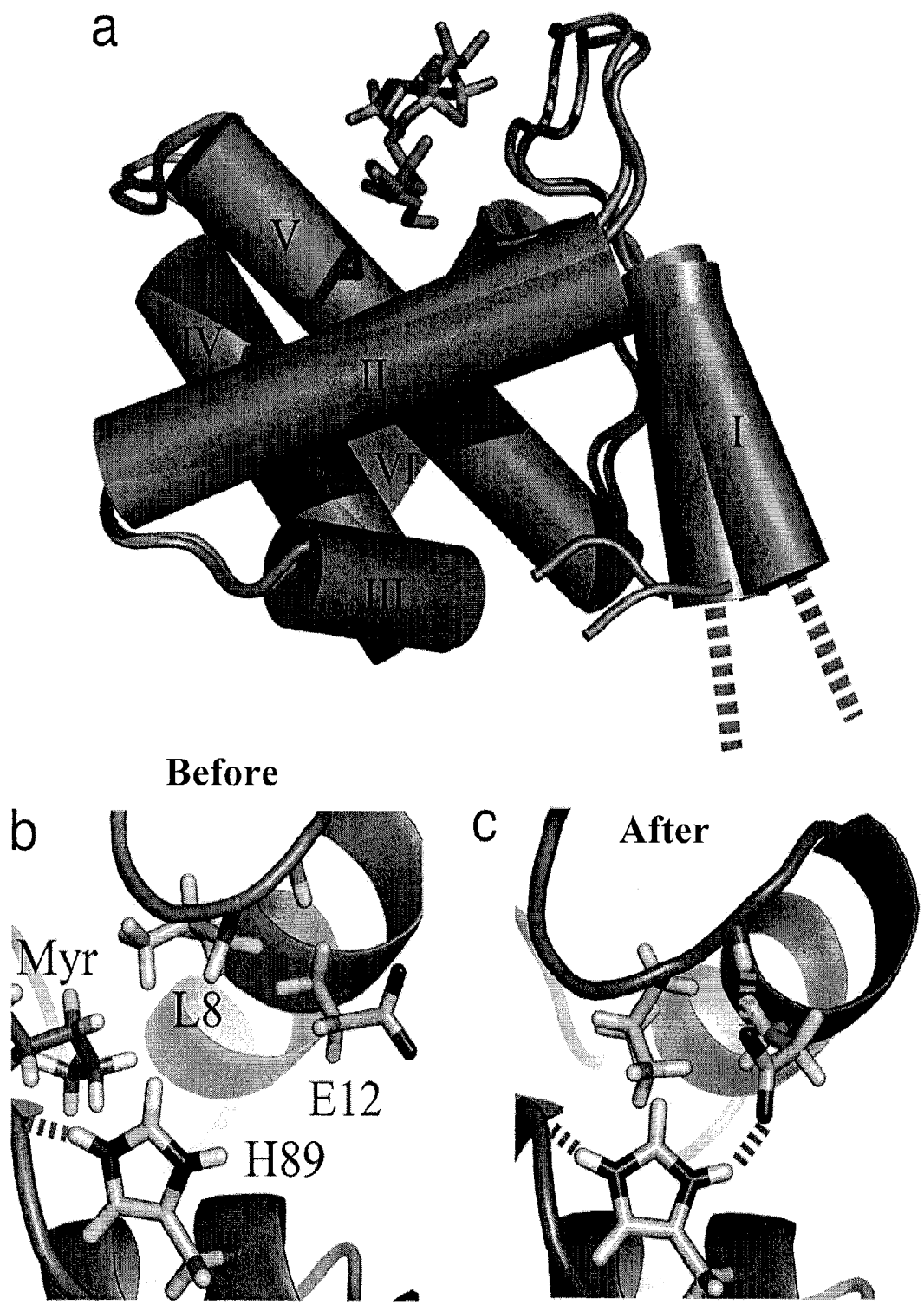
FIG. 6 shows the comparison of the myrMA structures before and after binding to di-$C_4$-PI(4,5)$P_2$. (a) Superposition showing that di-$C_4$-PI(4,5)$P_2$ binding induces only minor structural changes in the loop connecting helices I and II and much larger changes in the structure and shift of the orientation of helix I. (b) View of the N terminus of myr(s)MA showing the orientation of helix I and relative location of E-12 and H-89 residing on the edges of a cavity associated with sequestration of the myristyl group. (c) View of the N-terminal portion of the di-$C_4$-PI(4,5)$P_2$:myr(e)MA complex showing the packing and hydrogen-bonding interactions that stabilize the myr(e) conformation, wherein H-89 and E-12 side chains form a salt bridge to stabilize the myristyl group.

The binding of di-$C_4$-PI(4,5)$P_2$ to myrMA results in small local structural changes, as evidenced by very small changes in intraprotein NOE crosspeak patterns and intensities for residues Arg-20, Arg-22, Gly-25, and Gln-28 of the 3-hairpin. No changes in intraprotein NOEs were detected for residues of helices II and V. However, significant NMR spectral and structural changes were observed for residues Myr-1-Lys-18 of myrMA. Residues Ser-9-Lys-18, which form an α-helix in the absence of di-$C_4$-PI(4,5)$P_2$, form a more compact helix with $3_{10}$ character in the di-$C_4$-PI(4,5)$P_2$:myr(e)MA complex, with Leu-13 packing tightly against Trp-16. In addition, Glu-12, which is located near the N terminus of helix I and does not make long-range contacts in the free myr(s)MA protein, packs tightly against the side chain of Val-88 upon di-$C_4$-PI(4,5)$P_2$ binding. These changes enable the Glu-12 carboxyl group to form hydrogen bonds with the side-chain HJ2 proton of His-89 and the backbone NH of Ser-9, as shown in FIG. 6(b). In addition, the side chains of Leu-8 and Leu-13 are packed tightly against the side chain of Trp-16 and occupy space that was formerly occupied by the terminal $CH_3$ group of the myristate in the myr(s)MA structure (19). These structural elements are very similar to those observed in the myr(-)MA crystal structure (38). Myristate exposure thus appears to be triggered by an allosteric mechanism, in which PI(4,5)$P_2$ binding induces small conformational changes in the 1-hairpin that in turn lead to more significant changes in the structure and orientation of helix I. These changes reposition hydrophobic residues near the N terminus of helix I in a manner that displaces the myristyl group and stabilizes the myr(e)MA species, as shown in FIG. 6(c).

Example 4

Specificity of Phosphatidylinositide Binding

The above structural studies suggested that both hydrophobic and electrostatic interactions contribute to binding. To determine the specificity of binding, $^1$H-$^{15}$N HSQC titration experiments were conducted with di-$C_4$-PI containing other combinations of phosphate groups at biologically relevant positions. No detectable changes were observed in the NMR spectra of myrMA upon titration with phosphatidylinositides di-$C_4$-PI, di-$C_4$-PI(3)P, di-$C_4$-PI(4)P, and di-$C_4$-PI(5)P. di-$C_4$-phosphatidylcholine, which lacks the inositol head group, also does not bind myrMA. Interestingly, di-$C_4$-PI(3, 5)$P_2$, which differs from di-$C_4$-PI(4,5)$P_2$ only in the placement of a single phosphate, does not bind myrMA or trigger myristate exposure. In contrast, di-$C_4$-PI(3,4,5)$P_3$ binds myrMA with affinity similar to that of di-$C_4$-PI(4,5)$P_2$ (81±18 μM) and also triggers myristate exposure.

Example 5

Implications for the Mechanism of Membrane Targeting

Phosphatidylinositides comprise a class of differentially phosphorylated lipids that facilitate intracellular trafficking by establishing the identity of organelles. At least five phosphatidylinositides that differ in the number and position of attached phosphates are associated preferentially with Golgi [PI(4)P], early endosome [PI(3)P], late endosome [PI(3,5)$P_2$], and plasma [PI(4)P, PI(4,5)$P_2$, and PI(3,4,5)$P_3$] membranes (30). Cellular proteins that interact differentially with these species can thus be targeted to specific membranes, enabling spatial distribution of subcellular activities (30). PI(4,5)$P_2$ is considered a major landmark for proteins that need to associate with the PM (30), and it functions in the regulation of a variety of activities, including endocytosis, exocytosis, synaptic vesicle trafficking, and enzyme activation (31). Recent studies by Freed and coworkers (21) indicate that HIV-1 hijacks the phosphatidylinositide signaling system, and that PI(4,5)$P_2$ [and possibly PI(3,4,5)$P_3$] plays a critical role in targeting Gag to the PM.

The present studies demonstrate that PI(4,5)$P_2$ can function as both an allosteric trigger for myristate exposure and a direct membrane anchor, providing a simple mechanism for targeting Gag to membranes enriched in PI(4,5)$P_2$. That PI(3)P, PI(4)P, and PI(3,5)$P_2$ do not bind MA with significant affinity or trigger myristate exposure is consistent with observations that Gag localizes and assembles at the PMs of most infected cell types. Membrane discrimination by this thermodynamic mechanism does not necessarily require additional cellular trafficking machinery, although the possibility cannot be ruled out that other factors may be involved in trafficking events such as transient nuclear import/export (26, 28) or MVB targeting (22).

Figure 7:
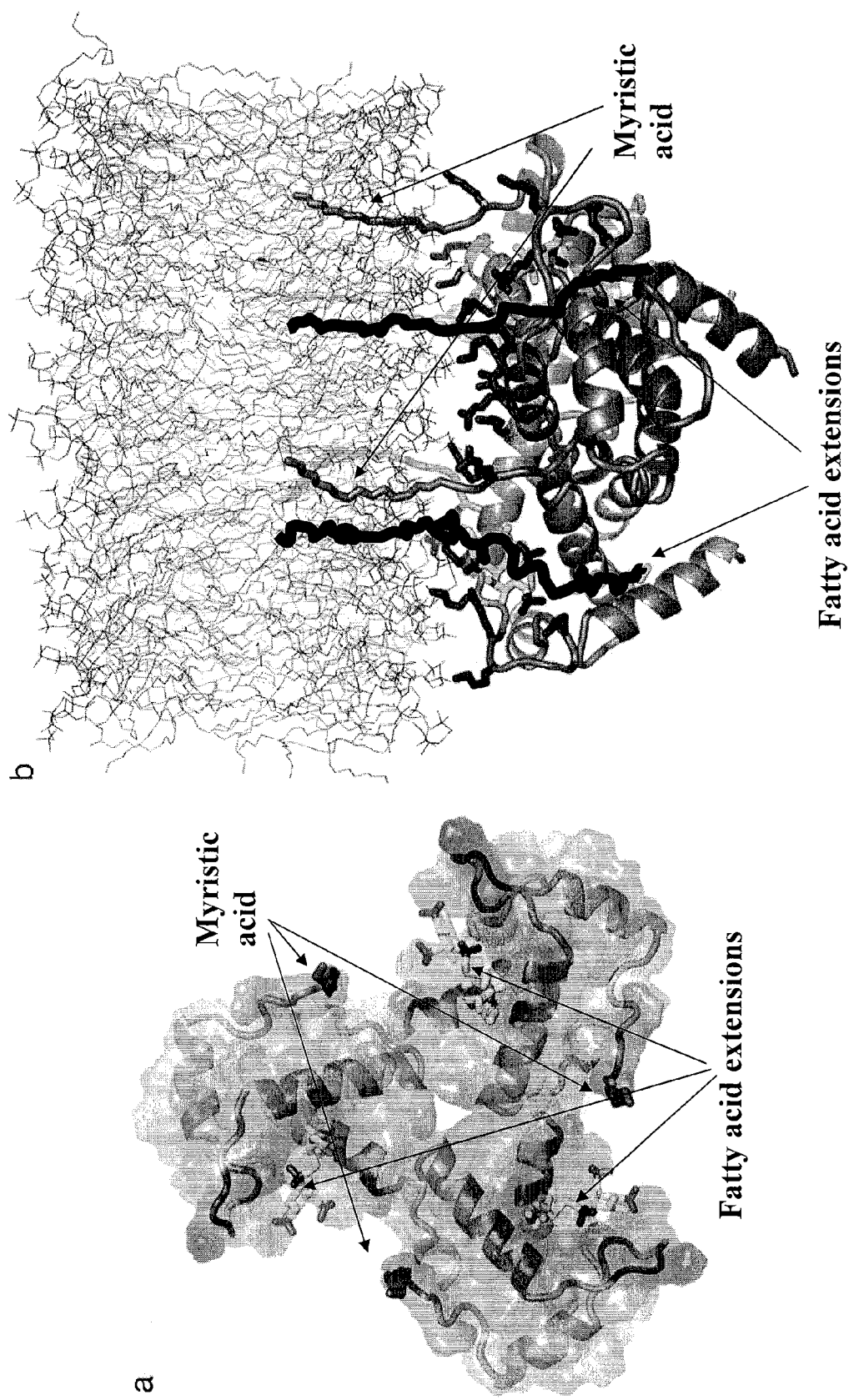
FIG. 7 shows membrane-binding model predicted from the structural studies. (a) Trimer model constructed by superpositioning three identical copies of myr(e)MA:di-$C_4$-PI(4,5)$P_2$ onto the coordinates of the trimeric of myr(−)MA x-ray structure (38) and substituting the 1'- and 2'-$C_8$ acyl chains by $C_{18}$ and $C_{20}$ acyl chains, respectively. The myristyl group and residues that contact the phosphatidylinositide are shown by arrows. (b) The exposed 1'-fatty acids and myristyl groups project from a highly basic surface (Arg and Lys sidechains shown by arrows) in a manner expected to synergistically promote membrane binding. The lipid model is from ref. 66.

The hydrophobic cleft that interacts with the 2'-acyl chain of di-$C_4$-PI(4,5)$P_2$ and di-$C_8$-PI(4,5)$P_2$ is capable of accommodating longer fatty acids without alteration of the protein structure, and a model of a trimeric PI(4,5)$P_2$:myrMA-membrane complex constructed by using 18- and 20-carbon 1'- and 2'-acyl chains, respectively, is shown in FIG. 7a. It is noteworthy that the lipid chains of PI(4,5)$P_2$ extend in opposite directions, with the 1'-chain inserted into the lipid bilayer and the 2'-chain sequestered by the protein (FIG. 7b). This conformation, and the predicted membrane-binding mode, are strikingly similar to those predicted in "extended lipid" phospholipid-cytochrome c models (41-43) and could be used to anchor other proteins to membranes as well (44). Although extrusion of the 2'-chain from lamellar membranes might intuitively be considered energetically expensive, a number of studies suggest this can actually relieve conformational stress caused by lipids with propensities for negative membrane curvature (41). Conformational dynamic studies also suggest that the 2'-chain is specifically favored for extrusion from the bilayer (44), and fluorescence quenching experiments indicate that the 2'-acyl chain of a brominated phospholipid is sequestered by cytochrome c upon binding to liposomes (43).

Confocal microscopy has shown that Gag molecules assemble at punctate sites on the PM (14), and there is considerable evidence that these sites comprise lipid raft microdomains (45-48). Lipid rafts contain elevated levels of cholesterol and sphingolipids with saturated fatty acids and form liquid-ordered membrane structures (49-51). Although PI(4,5)$P_2$ may inherently associate preferentially with lipid rafts, this hypothesis remains controversial (31). More recent studies suggest that PI(4,5)$P_2$ molecules are homogeneously dispersed within the PM of quiescent cells, and that they colocalize with lipid rafts upon stimulation by a mechanism that has yet to be identified (52). The findings of the present invention show that the 2'-acyl chain is sequestered by the protein and this suggests a potential mechanism for the lateral targeting of PI(4,5)$P_2$:Gag complexes to lipid raft microdomains. It is well known that rafts interact preferentially with saturated fatty acids (49-51). In fact, substitution of the saturated myristyl group of HIV-1 Gag by unsaturated lipids reduces the affinity of Gag for rafts, but not for membranes in general, and thereby inhibits particle assembly (53). Proteins that bind lipid rafts generally contain two saturated acyl chains or are anchored by adaptor molecules that contain two saturated chains (for example, glycosylphosphatidylinositol-anchored proteins; (48, 54). Because cellular phosphatidylinositides generally contain stearate, an 18-carbon saturated fatty acid, at the 1'-position, and arachidonate, a 20-carbon fatty acid with four nonconjugated double bonds, at the 2'-position, sequestration of the 2'-chain is likely to reduce the affinity of PI(4,5)$P_2$ for fluid regions of the membrane and promote its association with rafts. Differential sequestration of the acyl chains could serve as a general mechanism for the lateral retargeting of phosphatidylinositides within the membrane, such as that observed during PI(4,5)$P_2$-dependent microtubule assembly (52).

It has been previously demonstrated that myristate exposure in myrMA and myrMA-CA protein constructs can be promoted by concentration-dependent protein self association. Such a myristyl switch mechanism is consistent with a number of in vitro experimental observations. For example, mutations that inhibit Gag assembly also disrupt membrane binding (55-57), and C-terminal truncations lead to progressive decreases in both Gag multimerization and membrane affinity (58). In addition, the binding of Gag to nucleic acid templates, which promotes Gag self association (59-62), also enhances Gag interactions with membranes (63-65). The relative influence of Gag self association and PI(4,5)$P_2$ binding for triggering myristate exposure in vivo is not clear. It is possible that a fraction of viral Gag molecules interact with PI(4,5)$P_2$ at lipid rafts, and that this initial complex serves as a nucleation site for additional Gag molecules that bind to the membrane in a PI(4,5)$P_2$-independent (but Gag self-association-dependent) manner.

The PI(4,5)$P_2$-binding site is highly conserved among the 454 published strains of HIV-1, with Ser-77, Asn-80, and Lys/Arg-22 being strictly conserved; Leu-21, Trp-36, and Thr-97 substituted once, and Lys-27 substituted twice. In contrast, other exposed residues that do not participate in structure stabilization or PI(4,5)$P_2$ binding are often extensively substituted. For example, Lys-30 which exhibited PI(4,5)$P_2$-dependent protection in accessibility assays (32) is substituted by a nonbasic residue in 40% of the known HIV-1 isolates. Such high conservation may be necessary for sites that interact with cellular constituents, which do not undergo evolutionary changes on the timescale of viral replication. Thus, the PI(4,5)$P_2$-binding site is an attractive antiviral target.

Numerous modifications and variations of the above-described invention are expected to occur to those of skill in the art. Accordingly, only such limitations as appear in the appended claims should be placed thereon.

REFERENCES

The contents of all references cited herein are hereby incorporated by reference herein for all purposes.
1. Gheysen D., Jacobs E., de Foresta F., Thiriart C., Francotte M., Thines D., De Wilde M. *Cell*. 1989; 59:103-112.
2. Wills J., Craven R. *AIDS*. 1991; 5:639-654.
3. Freed E. O. *Virology*. 1998; 251:1-15.
4. Briggs J. A. G., Simon M. N., Gross I., Krausslich H.-G., Fuller S. D., Vogt V. M., Johnson M. C. *Nat. Struct. Mol. Biol.* 2004; 11:672-675.
5. Vogt V. M., Simon M. N. *J. Virol.* 1999; 73:7050-7055.
6. Bryant M., Ratner L. *Proc. Natl. Acad. Sci. USA*. 1990; 87:523-527.
7. Copeland N. G., Jenkins N. A., Nexo B., Schultz A. M., Rein A., Mikkelsen T., Jorgensen P. *J. Virol.* 1988; 62:479-487.
8. Gottlinger H. G., Sodroski J. G., Haseltine W. A. *Proc. Natl. Acad. Sci. USA*. 1989; 86:5781-5785.
9. Spearman P., Horton R., Ratner L., Kuli-Zade I. *J. Virol.* 1997; 71:6582-6592.
Spearman P., Wang J.-J., Vander Heyden N., Ratner L. *J. Virol.* 1994; 68:3232-3242.
11. Yuan X., Yu X., Lee T.-H., Essex M. *J. Virol.* 1993; 67:6387-6394
12. Freed E. O., Orenstein J. M., Buckler-White A. J., Martin M. A. *J. Virol.* 1994; 68:5311-5320.
13. Ono A., Orenstein J. M., Freed E. O. *J. Virol.* 2000; 74:2855-2866.
14. Hermida-Matsumoto L., Resh M. D. *J. Virol.* 2000; 74:8670-8679.
15. Zhou W., Resh M. D. *J. Virol.* 1996; 70:8540-8548.
16. Paillart J.-C., Gottlinger H. G. *J. Virol.* 1999; 73:2604-2612.

17. Hermida-Matsumoto L., Resh M. D. *J. Virol.* 1999; 73:1902-1908.
18. Bouamr F., Scarlata S., Carter C. A. *Biochemistry.* 2003; 42:6408-6417.
19. Tang C., Loeliger E., Luncsford P., Kinde I., Beckett D., Summers M. F. *Proc. Natl. Acad. Sci. USA.* 2004; 101:517-522.
20. Cannon P. M., Matthews S., Clark N., Byles E. D., Iourin O., Hockley D. J., Kingsman S., Kingsman A. *J. Virol.* 1997; 71:3474-3483.
21. Ono A., Ablan S. D., Lockett S. J., Nagashima K., Freed E. O. *Proc. Natl. Acad. Sci. USA.* 2004; 101:14889-14894.
22. Dong X., Li H., Derdowski A., Ding L., Burnett A., Chen X., Peters T. R., Dermody T. S., Woodruff E., Wang J.-J., Spearman P. *Cell.* 2005; 120:663-674.
23. Nguyen D. G., Booth A., Gould S. J., Hildreth J. E. *J. Biol. Chem.* 2003; 278:52347-52354.
24. Ono A., Freed E. O. *J. Virol.* 2004; 78:1552-1563.
25. Raposo G., Moore M., Innes D., Leijendekker R., Leigh-Brown A., Benaroch P., Geuze H. *Traffic.* 2002; 3:718-729.
26. Dupont S., Sharova N., DeHoratius C., Virbasius C.-M. A., Zhu X., Bukrinskaya A. G., Stevenson M., Green M. R. *Nature.* 1999; 402:681-685.
27. Scheifele L. Z., Ryan E. P., Parent L. J. *J. Virol.* 2005; 79:8732-8741.
28. Scheifele L. Z., Garbitt R. A., Rhoads J. D., Parent L. J. *Proc. Natl. Acad. Sci. USA.* 2002; 99:3944-3949.
29. Martin T. F. J. *Curr. Opin. Cell Biol.* 2001; 13:493-499.
30. Behnia R., Munro S, *Nature.* 2005; 438:597-604.
31. McLaughlin S., Murray D. *Nature.* 2005; 438:605-611.
32. Shkriabai N., Datta S. K., Zhao Z., Hess S., Rein A., Kvaratskhelia M. *Biochemistry.* 2006; 45:4077-4083.]
33. Campbell S., Fisher R. J., Towler E. M., Fox S., Issaq H. J., Wolfe T., Phillips L. R., Rein A. *Proc. Natl. Acad. Sci. USA.* 2001; 98:10875-10879.
34. Janmey P. A., IIda K., Yin H. L., Stossel T. P. *J. Biol. Chem.* 1987; 262:12228-12236.
35. Dudley D. T., Spector A. A. *Biochem. J.* 1986; 236:235-242.
36. Kutateladze T., Overduin M. *Science.* 2001; 291:1793-1796.
37. Massiah M. A., Starich M. R., Paschall C., Summers M. F., Christensen A. M., Sundquist W. I. *J. Mol. Biol.* 1994; 244:198-223.
38. Hill C. P., Worthylake D., Bancroft D. P., Christensen A. M., Sundquist W. I. *Proc. Natl. Acad. Sci. USA.* 1996; 93:3099-3104.
39. Wütthrich, K. NMR of Proteins and Nucleic Acids. New York: Wiley; 1986.
40. Kay L. E., Clore G. M., Bax A., Gronenborn A. M. *Science.* 1990; 249:411-414.
41. Kinnunen P. K. J., Koiv A., Lehtonen J. Y. A., Rytomaa M., Mustonen P. *Chem. Phys. Lipids.* 1994; 73:181-207.
42. Rytomaa M., Kinnunen P. K. J. *J. Biol. Chem.* 1995; 270:3197-3202.
43. Touminen E. K. J., Wallace C. J. A., Kinnunen P. K. J. *J. Biol. Chem.* 2002; 277:8822-8826.
44. Kinnunen P. K. J. Chem. Phys. Lipids. 1996; 81:151-166.
45. Aloia R. C., Tian H., Jensen F. C. *Proc. Natl. Acad. Sci. USA.* 1993; 90:5181-5185.
46. Ono A., Freed E. O. *Proc. Natl. Acad. Sci. USA.* 2001; 98:13925-13930.
47. Nguyen D. H., Hildreth J. E. *J. Virol.* 2000; 74:3264-3272.
48. Ono A., Freed E. O. *Adv. Virus Res.* 2005; 64:311-358.
49. Brown D. A., London E. *Biochem. Biophys. Res. Commun.* 1997; 240:1-7.
50. Zacharias D. A., Violin J. D., Newton A. C., Tsien R. Y. *Science.* 2002; 296:913-916.
51. Melkonian K. A., Ostermeyer A. G., Chen J. Z., Roth M. G., Brown D. A. *J. Biol. Chem.* 1999; 274:3910-3917.
52. Golub T., Caroni P. *J. Cell Biol.* 2005; 169:151-162.
53. Lindwasser O. W., Resh M. D. *Proc. Natl. Acad. Sci. USA.* 2002; 99:13037-13042.
54. Brown D. A., London E. *J. Biol. Chem.* 2000; 275:17221-17224.
55. Ebbets-Reed D., Scarlata S., Carter C. A. *Biochemistry.* 1996; 35:14268-14275.
56. Liang C., Hu J., Russell R. S., Roldan A., Kleiman L., Wainberg M. A. *J. Virol.* 2002; 76: 11729-11737.
57. Accola M. A., Hoglund S., Gottlinger H. G. *J. Virol.* 1998; 72:2072-2078.
58. Ono A., Demirov D., Freed E. O. *J. Virol.* 2000; 74:5142-5150.
59. Feng Y.-X., Li T., Campbell S., Rein A. *J. Virol.* 2002; 76:11757-11762.
60. Campbell S., Vogt V. M. J. Virol. 1995; 69:6487-6497.
61. Muriaux D., Mirro J., Harvin D., Rein A. *Proc. Natl. Acad. Sci. USA.* 2001; 98:5246-5251.
62. Yu F., Joshi S. M., Ma Y. M., Kingston R. L., Simon M. N., Vogt V. M. *J. Virol.* 2001; 75:2753-2764.
63. Platt E. J., Haffar O. K. *Proc. Natl. Acad. Sci. USA.* 1994; 91:4594-4598.
64. Sandefur S., Varthakavi V., Spearman P. *J. Virol.* 1998; 72:2723-2732.
65. Sandefur S., Smith R. M., Varthakavi V., Spearman P. *J. Virol.* 2000; 74:7238-7249.
66. Heller H., Schaefer M., Schulten K. *J. Phys. Chem.* 1993; 97:8343-8360.

That which is claimed is:

1. An in vitro testing method in a host cell to determine compounds that inhibit the binding of phosphatidylinositol (PI)4,5-bisphosphate (PI(4,5)P$_2$) with the MA domain of an HIV Gag protein comprising:
    (a) introducing into the host cell a detectable tag to be triggered by positional changes of amino acid residues in the MA domain of the HIV Gag protein;
    (b) contacting a test compound with PI(4,5)P$_2$ and the MA domain of the HIV Gag protein; and
    (c) measuring a signal from the detectable tag to determine the ability of the test compound to change positioning of amino acid residues in the MA domain flanked by amino acid residues His-89 and Glu-12 or reducing the interaction of the amino acid residues His-89 and Glu-12 from forming a salt bridge.

2. The testing method according to claim 1, wherein the test a binding assay.

3. The testing method according to claim 1, wherein the host cell is a human CD4$^+$ T cell, CHO cell, or 293 cell.

4. The testing method according to claim 3, wherein the host cell has been transformed for expression of at least the MA domain of HIV Gag.

5. The testing method according to claim 1, wherein the PI(4,5)P$_2$ or a fragment thereof is positioned on the plasma membrane of the host cell.

6. The testing method according to claim 1, wherein the testing compound is selected from a library of synthetic or natural compounds.

7. The testing method according to claim 1, wherein reduction in triggering of the detectable tag provides for an inhibitory testing agent, wherein the detectable tag is triggered when a salt bridge is formed between amino acid residues His-89 and Gly-12.

8. The testing method according to claim 4, wherein the detectable tag comprises radiolabeled amino acid residues on the MA domain of a HIV Gag protein and monitoring signals associated with myr exposure, wherein the amino acid residue is selected from Gly 10, Gly 11, Ser 6, His-89, Gly-12 and a combination thereof.

9. An in vitro screening method to determine compounds that inhibit the binding of phosphatidylinositol (PI)4,5-biphosphate (PI(4,5)P$_2$) with the MA domain of an HIV Gag protein that comprises at least two components and a testing agent, the method comprising:
 (a) providing in a host cell a first component comprising a PI(4,5)P$_2$ molecule positioned within a lipid layer and a second component comprising the HIV Gag MA domain protein or a fragment thereof, wherein the Gag protein has been previously introduced into the cell via an expression vector for expression within the host cell;
 (b) providing in said host cell a reporter tag, wherein the reporter tag is triggered by the interaction between PI(4,5)P$_2$ molecule and the MA domain wherein such interaction causes a positional change in amino acid residues positioned on the MA domain;
 (c) allowing said PI(4,5)P$_2$ molecule and MA domain to interact with each other within said host cell in the presence of a test compound; and
 (d) determining the presence or absence of a triggering of the reporter tag, wherein reduction in triggering of the reporter tag provides for an inhibitory testing agent that reduces binding between PI(4,5)P$_2$ molecule and the MA domain by changing positioning of amino acid residues in the MA domain flanked by amino acid residues His-89 and Glu-12 or reducing the interaction of the amino acid residues His-89 and Glu-12 from forming a salt bridge.

10. The in vitro screening method of claim 9, wherein the positional change is in His-89 and Gly-12.

* * * * *